US010959939B2

(12) United States Patent
Freitag et al.

(10) Patent No.: US 10,959,939 B2
(45) Date of Patent: Mar. 30, 2021

(54) LIQUID PHARMACEUTICAL COMPOSITION OF ETANERCEPT WITH LYSINE AND PROLINE

(71) Applicant: ARES TRADING S.A., Aubonne (CH)

(72) Inventors: Angelika Freitag, Martinsried (DE); Andrea Hawe, Martinsried (DE); Gianluca Rinaldi, Monterotondo (IT); Alessandra Del Rio, Rome (IT)

(73) Assignee: ARES TRADING S.A., Aubonne (CH)

( * ) Notice: Subject to any disclaimer, the term of this patent is extended or adjusted under 35 U.S.C. 154(b) by 43 days.

(21) Appl. No.: 15/536,941

(22) PCT Filed: Dec. 17, 2015

(86) PCT No.: PCT/EP2015/080326
§ 371 (c)(1),
(2) Date: Jun. 16, 2017

(87) PCT Pub. No.: WO2016/102328
PCT Pub. Date: Jun. 30, 2016

(65) Prior Publication Data
US 2017/0348225 A1 Dec. 7, 2017

(30) Foreign Application Priority Data
Dec. 22, 2014 (EP) .................................. 14199871

(51) Int. Cl.
| | | |
|---|---|---|
| *C07K 14/705* | (2006.01) | |
| *C07K 19/00* | (2006.01) | |
| *A61K 38/17* | (2006.01) | |
| *A61K 47/18* | (2017.01) | |
| *A61K 9/00* | (2006.01) | |
| *A61K 47/26* | (2006.01) | |
| *A61K 9/08* | (2006.01) | |
| *A61K 47/06* | (2006.01) | |
| *C07K 14/715* | (2006.01) | |

(52) U.S. Cl.
CPC ............. *A61K 9/0019* (2013.01); *A61K 9/08* (2013.01); *A61K 38/1793* (2013.01); *A61K 47/06* (2013.01); *A61K 47/18* (2013.01); *A61K 47/183* (2013.01); *A61K 47/26* (2013.01); *C07K 14/70578* (2013.01); *C07K 14/7151* (2013.01); *C07K 19/00* (2013.01); *C07K 2319/03* (2013.01); *C07K 2319/30* (2013.01)

(58) Field of Classification Search
CPC ............ C07K 14/7151; A61K 38/1793; A61K 47/183
See application file for complete search history.

(56) References Cited

U.S. PATENT DOCUMENTS

| | | | |
|---|---|---|---|
| 5,605,690 A | 2/1997 | Jacobs et al. | |
| 7,276,477 B2 | 10/2007 | Osslund et al. | |
| 9,700,595 B2 * | 7/2017 | Lee .......................... | A61K 9/08 |
| 2013/0101584 A1 | 4/2013 | Manning et al. | |

FOREIGN PATENT DOCUMENTS

| | | | |
|---|---|---|---|
| WO | 9103553 A1 | 3/1991 | |
| WO | 9406476 A1 | 3/1994 | |
| WO | 03072060 A2 | 9/2003 | |
| WO | 2011141926 A2 | 11/2011 | |
| WO | 2012143418 A1 | 10/2012 | |
| WO | 2012165914 A2 | 12/2012 | |
| WO | 2012165917 A1 | 12/2012 | |
| WO | 2013006454 A1 | 1/2013 | |
| WO | WO-2014078627 A1 * | 5/2014 | ......... C07K 14/7151 |
| WO | 2014178216 A1 | 11/2014 | |

OTHER PUBLICATIONS

Jones et al., "Structure of Tumour Necrosis Factor," Nature, Mar. 16, 1989, pp. 225-228, vol. 338.
Pennica et al., "Human Tumour Necrosis Factor: Precursor Structure, Expression and Homology to Lymphotoxin," Nature, Dec. 1984, pp. 724-729, vol. 312.
Davis et al., "Structure of Human Tumor Necrosis Factor Alpha Derived from Recombinant DNA," American Chemical Society, Biochemistry, Oct. 1987, pp. 1322-1326, vol. 26, No. 5.
Nanda et al., "Etanercept: A Clinical Review of Current and Emerging Indications," Expert Opinion on Pharmacotherapy, Mar. 2005, pp. 1175-1186, vol. 5, No. 5, DOI: 10.1517/14656566.5.5.1175.
Goffe et al., "Etanercept: An Overview," J. Am. Acad. Dermatol., Aug. 2003, S105-S111, vol. 49, No. 2.
International Search Report dated Feb. 22, 2016 in corresponding International Application No. PCT/EP2015/080326, 6 pages.

\* cited by examiner

*Primary Examiner* — Zachary C Howard
(74) *Attorney, Agent, or Firm* — Carter, DeLuca & Farrell LLP

(57) ABSTRACT

The present invention relates to novel liquid protein formulations, particularly arginine-free liquid pharmaceutical compositions of etanercept. The invention employs particular combinations and classes of buffer systems, tonicifiers, and sugar stabilisers, optionally alongside polar ionisable amino acids (e.g. aspartic acid, glutamic acid, histidine, and lysine), to afford a viable and storable drug product.

10 Claims, No Drawings

LIQUID PHARMACEUTICAL COMPOSITION OF ETANERCEPT WITH LYSINE AND PROLINE

INTRODUCTION

The present invention relates to a novel liquid protein formulation. In particular, the invention relates to a liquid pharmaceutical composition of etanercept, to a method of manufacturing the composition, to a kit including the composition, to a package including the composition, to a method of manufacturing the package, and to methods of treatment using the composition and/or package.

BACKGROUND

Treatment of tumour necrosis factor-alpha (TNF-α)-related autoimmune diseases, such as rheumatoid arthritis (including juvenile rheumatoid arthritis), psoriatic arthritis, plaque psoriasis, and ankylosing spondylitis, has been achieved through the use of FDA-approved drugs such as Etanercept (ENBREL®, Amgen, Wyeth)—CAS Registry Number: 185243-69-0; CAS Name: 1-235-Tumor necrosis factor receptor (human) fusion protein with 236-467-immunoglobulin G1 (human g1-chain Fc fragment)). In particular, Etanercept is a recombinant fusion protein containing the human soluble TNF receptor p75 linked to the Fc portion of human immunoglobulin G1, which dimerizes via the cysteine residues in the Fc fragment to form an immunoglobulin-like structure. It's preparation and uses have been previously described in the literature, including WO91/03553 and WO 9406476 and U.S. Pat. No. 5,605,690 (all Immunex), whilst its clinical use is reviewed in B. Goffe, J. C. Cather, *J. Am. Acad. Dermatol.* 49, S105-S111 (2003); S. Nanda, J. M. Bathon, *Expert Opin. Pharmacother.* 5, 1175-1186 (2004). Etanercept's TNFα-inhibiting properties are believed to be responsible for its clinical effects.

Initially, due to storage stability issues, etanercept (Enbrel®) was provided to medical practitioners and/or patients in multiple-use vials as a sterile, white, preservative-free, lyophilized powder for reconstitution with 1 mL of supplied sterile water for injection containing 0.9% benzyl alcohol prior to subcutaneous injection. Reconstituted solutions had a pH of about 7.4 and were clear and colourless. Each vial contained 25 mg etanercept, 40 mg mannitol, 10 mg sucrose, and 1.2 mg tromethamine.

However, due to the inconvenience of reconstitution to medical practitioners and end-users alike, more stable liquid formulations were developed (see WO03/072060—Immunex) which could be stored for a period of time in single-use preloaded syringes which could be used directly for administration of etanercept via subcutaneous injection. Such liquid formulations of etanercept (Enbrel®) comprise an aqueous solution of 50 mg/mL etanercept, 1% w/v sucrose, 100 mM sodium chloride, 25 mM sodium phosphate, 25 mM L-arginine hydrochloride, having a pH of about 6.3. As explained in WO03/072060, the presence of L-arginine was deemed essential for the stability and viability of the etanercept fusion protein, in particular to prevent aggregation. WO03/072060 describes various analyses, including Size Exclusion Chromatography (SEC), Hydrophobic Interaction Chromatography (HIC), Sodium dodecylsulfate-polyacrylamide gel electrophoresis (SDS-PAGE), to illustrate the effectiveness of L-arginine as an antiaggregant for etanercept.

The elusiveness of viable and stable alternative liquid formulations of etanercept has stimulated interest amongst a variety of researchers. For instance, more recent publications such as WO2011141926 (Intas) describe alternative etanercept liquid formulations which employ a complex array of excipients, including inter alia surfactants and chelators. WO2012165914 (LG Life Sciences) describes alternative etanercept liquid formulations in which sulphur-containing amino acids were considered as possible stabilisers of etanercept. WO2013006454 (Biogen) describes another alternative etanercept liquid formulation in which L-arginine is replaced by a high salt content.

Despite a significant amount of research activity in this area, stable and viable arginine-free formulations still remain highly elusive, no doubt due to the delicate interplay of factors effecting the stability of such formulations. However, L-arginine is desirably avoided, especially in injectable formulations, in view of its well known side effects, including anaphylaxis, hyperchloremic metabolic acidosis, cerebral edema, hyperkalemia, incompatibilities with certain other classes of drugs (e.g. phosphodiesterase inhibitors such as sildenafil/Viagra®), bloating, diarrhea, hematuria, hives, hormonal changes, increased blood urea nitrogen, serum creatine and serum creatinine, increased inflammatory response (e.g. in people with asthma or cystic fibrosis), leg restlessness, lower back pain, nausea, night sweats and flushing (e.g. with arginine withdrawal), numbness (especially with arginine-containing injections), rash, reduction in hematocrit, severe tissue damage (especially with arginine-containing injections), stomach and intestine discomfort, systemic acidosis, and venous irritation.

There is therefore a need for an alternative or improved liquid formulation of etanercept. Desirably, any new formulations would solve at least one of the aforementioned problems and/or at least one problem inherent in the prior art, and may suitably solve two or more of said problems. Desirably, any new formulations would avoid or minimise the emergence of other problems. Desirably, the problem(s) of the prior art may be solved whilst reducing the complexity of the formulation.

SUMMARY OF THE INVENTION

According to a first aspect of the present invention there is provided a liquid pharmaceutical composition comprising etanercept (which suitably includes any biosimilar thereof); a buffer system (or buffering agent); a tonicifier; and a sugar stabiliser. The composition suitably comprises (or excludes) any one or more additional components defined herein in relation to a liquid pharmaceutical composition (e.g. including one or more particular amino acids; excluding arginine, etc.), optionally in any amount, concentration, or form stipulated herein. The composition suitably exhibits any one or more parameters or properties given herein in relation to a liquid pharmaceutical composition (e.g. pH, osmolality, aggregation, fragmentation, protein unfolding, turbity, etc.).

According to a second aspect of the present invention there is provided a package (e.g. pre-filled syringe, pen, intravenous bag, or a package/container containing any of the aforementioned) comprising a liquid pharmaceutical composition as defined herein.

According to a third aspect of the present invention there is provided a drug delivery device (e.g. pre-filled syringe or pen, or intravenous bag) comprising a liquid pharmaceutical composition as defined herein.

According to a fourth aspect of the present invention there is provided a kit of parts comprising a drug delivery device, a liquid pharmaceutical composition (or two or more parts thereof which, when reconstituted, together produce the liquid pharmaceutical composition) as defined herein (optionally contained in a package or container), and optionally a set of instructions with directions regarding the administration (e.g. sub-cutaneous) of the liquid pharmaceutical composition.

According to an fifth aspect of the present invention there is provided a method of manufacturing a liquid pharmaceutical composition, the method comprising mixing together etanercept (which suitably includes any biosimilar thereof); a buffer system (or buffering agent); a tonicifier; and a sugar stabiliser; and optionally any one or more additional components defined herein in relation to a liquid pharmaceutical composition, optionally in any amount, concentration, or form stipulated; and optionally adjusting any one or more parameters given herein in relation to a liquid pharmaceutical composition (e.g. pH, osmolality).

According to a sixth aspect of the present invention there is provided a liquid pharmaceutical composition obtainable by, obtained by, or directly obtained by a method of manufacturing a liquid pharmaceutical composition as defined herein.

According to a seventh aspect of the present invention there is provided a method of manufacturing a package or a drug delivery device, the method comprising incorporating a liquid pharmaceutical composition as defined herein within a package or drug delivery device.

According to an eighth aspect of the present invention there is provided a package or a drug delivery device obtainable by, obtained by, or directly obtained by a method of manufacturing a package or a drug delivery device as defined herein.

According to a ninth aspect of the present invention there is provided a method of treating a disease or medical disorder in a patient in need of such treatment, said method comprising administering to said patient a therapeutically effective amount of a liquid pharmaceutical composition as defined herein.

According to a tenth aspect of the present invention there is provided a liquid pharmaceutical composition as defined herein for use in therapy.

According to an eleventh aspect of the present invention there is provided a use of a liquid pharmaceutical composition as defined herein in the manufacture of a medicament for the treatment of a disease or disorder.

According to a twelfth aspect of the present invention there is provided a method of treating a tumour necrosis factor-alpha (TNF-α)-related autoimmune disease in a patient in need of such treatment, said method comprising administering to said patient a therapeutically effective amount of a liquid pharmaceutical composition as defined herein.

According to a thirteenth aspect of the present invention there is provided a liquid pharmaceutical composition as defined herein for use in the treatment of a tumour necrosis factor-alpha (TNF-α)-related autoimmune disease.

According to a fourteenth aspect of the present invention there is provided a use of a liquid pharmaceutical composition as defined herein in the manufacture of a medicament for the treatment of a tumour necrosis factor-alpha (TNF-α)-related autoimmune disease.

According to a fifteenth aspect of the present invention there is provided a method of treating rheumatoid arthritis, juvenile rheumatoid arthritis, psoriatic arthritis, plaque psoriasis, and/or ankylosing spondylitis in a patient in need of such treatment, said method comprising administering to said patient a therapeutically effective amount of a liquid pharmaceutical composition as defined herein.

According to a sixteenth aspect of the present invention there is provided a liquid pharmaceutical composition as defined herein for use in the treatment of rheumatoid arthritis, juvenile rheumatoid arthritis, psoriatic arthritis, plaque psoriasis, and/or ankylosing spondylitis.

According to a seventeenth aspect of the present invention there is provided a use of a liquid pharmaceutical composition as defined herein in the manufacture of a medicament for the treatment of rheumatoid arthritis, juvenile rheumatoid arthritis, psoriatic arthritis, plaque psoriasis, and/or ankylosing spondylitis.

In further aspects, the invention provides a liquid pharmaceutical composition, a package, a drug delivery device, a kit of parts, a method of manufacturing a liquid pharmaceutical composition, a method of manufacturing a package or a drug delivery device, a method of treating, a liquid pharmaceutical composition for use, and a use of a liquid pharmaceutical composition in the manufacture of a medicament, essentially as defined herein (including in any of the aforementionied twenty aspects) except that, rather than being specific to "etanercept" (and biosimilars thereof), the invention may instead apply (and thereby be defined as relating) to any TNF-α-inhibiting protein, including a fusion protein, antibody (anti-TNF-α antibody), antibody fragment, or any biosimilar thereof, albeit most suitably a fusion protein that inhibits human TNF-α activity. Suitably the fusion protein is a therapeutically effective medicament (at least when administered in appropriate quantities to a patient in need thereof) (or a biosimlar thereof—see below for definitions of biosimilars in relation to etanercept, which applies equally to all TNFα-inhibiting proteins), suitably one which has received FDA approval. As such, any reference herein to "etanercept" may, unless incompatible therewith, be construed as a reference to any TNFα-inhibiting protein for the purpose of these additional aspects of the invention (whether this relates to absolute or relative amounts, concentrations, parameters, or properties, or whether it relates to certain definitions, such as what constitutes a biosimilar).

One of these further aspects of the present invention provides a liquid pharmaceutical composition comprising a TNFα-inhibiting protein (which suitably includes any biosimilar thereof); a buffer system (or buffering agent); a tonicifier; and a sugar stabiliser; wherein the composition optionally comprises (or excludes) any one or more additional components defined herein in relation to a liquid pharmaceutical composition (e.g. including one or more particular amino acids; excluding arginine, etc.), optionally in any amount, concentration, or form stipulated herein; and wherein the composition optionally exhibits any one or more parameters or properties given herein in relation to a liquid pharmaceutical composition (e.g. pH, osmolality, aggregation, fragmentation, protein unfolding, turbity, etc.).

Suitably the TNFα-inhibiting protein treats inflammation. Suitably the TNFα-inhibiting protein may be used to treat rheumatoid arthritis, juvenile rheumatoid arthritis, psoriatic arthritis, plaque psoriasis, ankylosing spondylitis, inflammatory bowel disease, psoriasis, hidradenitis suppurativa and refractory asthma. In a particular embodiment, the TNFα-inhibiting protein is selected from a fusion protein and a monoclonal antibody. In a particular embodiment the fusion protein is etanercept. In a particular embodiment, the monoclonal antibody is selected from the group consisting of infliximab, adalimumab and certolizumab pegol.

Any features, including optional, suitable, and preferred features, described in relation to any particular aspect of the invention may also be features, including optional, suitable and preferred features, of any other aspect of the present invention.

DETAILED DESCRIPTION OF THE INVENTION

Definitions

Unless otherwise stated, the following terms used in the specification and claims have the following meanings set out below.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

For the avoidance of doubt, it is hereby stated that the information described earlier in this specification under the heading "Background" is relevant to the invention and is to be read as part of the disclosure of the invention.

Suitably, unless stated otherwise, where reference is made to a parameter (e.g. pH, pKa, etc.) or state of a material (e.g. liquid, gas, etc.) which may depend on pressure and/or temperature, suitably in the absence of further clarification such a reference refers to said parameter at standard ambient temperature and pressure (SATP). SATP is a temperature of 298.15 K (25° C., 77° F.) and an absolute pressure of 100 kPa (14.504 psi, 0.987 atm).

Unless stated otherwise, any reference herein to an "average" value is intended to relate to the mean value.

References herein to "etanercept" include the drug substance commercially available as Enbrel®, as well as etanercept as defined in WO91/03553 and WO 9406476 and U.S. Pat. No. 5,605,690 (all Immunex) and elsewhere in the art, and also biosimilars thereof. Etanercept is a homodimeric fusion protein formed from the combination of two soluble human 75-kilodalton TNF receptors each linked to an Fc portion of an IgG1. Etanercept is suitably produced by recombinant DNA. This suitably fuses the TNF receptor to the Fc portion of the IgG1 antibody. The relevant recombinant DNA may be produced by isolating the DNA sequence that encodes the human gene for soluble TNF receptor 2 (i.e. a receptor that binds to TNFα); and also the DNA sequence that encodes the human gene for the Fc portion of IgG1; before linking these two DNA sequences together. The linked DNA sequence is then expressed to yield a protein containing the protein sequence for the soluble fragment of the TNF receptor 2 linked to the protein for IgG1 Fc. The sequence listing for the monomeric component of etanercept, and a method of forming a crystalline form thereof, is also disclosed in U.S. Pat. No. 7,276,477 (identified therein as SEQ ID NO: 4). Dimers of of these fusion proteins are formed when monomers are held together by three disulfide bonds that form between the immunoglobulin portions of the two monomers.

References herein to "etanercept" may include biosimilars which, for instance, may share at least 75%, suitably at least 80%, suitably at least 85%, suitably at least 90%, suitably at least 95%, suitably at least 96%, suitably at least 97%, suitably at least 98% or most suitably at least 99% protein sequence identity with any one of protein sequences disclosed in the art relating to etanercept. Alternatively or additionally, references herein to "etanercept" may include biosimilars which exhibit at least 75%, suitably at least 80%, suitably at least 85%, suitably at least 90%, suitably at least 95%, suitably at least 96%, suitably at least 97%, suitably at least 98% or most suitably at least 99% protein sequence homology with any one of protein sequences disclosed in the art relating to etanercept. Alternatively or additionally, a biosimilar may have a (slightly) different glycosylation profile, even if the protein sequence is substantially the same or different to the extent specified above.

Herein, etanercept employed in the compositions and methods of the invention are suitably "substantially purified", suitably meaning that the etanercept is a polypeptide that is substantially free of other polypeptides present in the environment in which it naturally occurs or in which it was produced; a preparation of a polypeptide that has been substantially purified contains at least 90% by weight (or at least 95%, at least 98%, or at least 99% by weight) of that polypeptide, wherein the weight of the polypeptide includes any carbohydrate, lipid, or other residues covalently attached to the polypeptide. A substantially purified polypeptide preparation may contain variation among polypeptide molecules within the preparation, with respect to extent and type of glycosylation or other post-translation modification, or with respect to conformation or extent of multimerization.

The term "biosimilar" (also know as follow-on biologics) is well known in the art, and the skilled person would readily appreciate when a drug substance would be considered a biosimilar of etanercept. Furthermore, such "biosimilars" would need to be officially approved as a "biosimilar" for marketing before said "biosimilar" is sold on the open market. The term "biosimilar" is generally used to describe subsequent versions (generally from a different source) of "innovator biopharmaceutical products" ("biologics" whose drug substance is made by a living organisim or devived from a living organism or through recombinant DNA or controlled gene expression methodologies) that have been previously officially granted marketing authorisation. Since biologics have a high degree of molecular complexity, and are generally sensitive to changes in manufacturing processes (e.g. if different cell lines are used in their production), and since subsequent follow-on manufacturers generally do not have access to the originators molecular clone, cell bank, know-how regarding the production process, nor to the active drug substance itself (only the innovator's commercialized drug product), any "biosimilar" may not be exactly the same as the innovator drug product.

For the purposes of various molar calculations (e.g. for molar ratios between etanercept and another component of the liquid pharmaceutical composition of the invention) the molecular weight of etanercept may be taken to be 51234.90 g/mol (reference molecular weight) based on details disclosed on the CAS database for CAS Registry Number: 185243-69-0, Etanercept, where the molecular formula is taken as $C_{2224}H_{3475}N_{621}O_{698}S_{36}$. As such, a liquid pharmaceutical composition containing 50 mg/mL etanercept may be considered a 0.976 mM (or 976 µM) solution of etanercept. This is not intended to be in any way limiting regarding the nature of any biosimilars of etanercept covered by the scope of the present invention, nor the level of glycosylation, either of which may effect the actual molecular weight. However, where a biosimilar does have a different molecular weight, the abovementioned reference molecular weight should be suitably used for the purposes of assessing whether or not such a biosimilar falls within the scope of any molar definitions stipulated within this specification. So the number of moles in a known weight of said biosimilar should be calculated, just for the purposes of this invention, using the above reference molecular weight.

Herein, the term "buffer" or "buffer solution" refers to a generally aqueous solution comprising a mixture of an acid (usually a weak acid, e.g. phosphoric acid or one or more hydrogenphosphate species) and its conjugate base (e.g. a phosphate, for example, sodium phosphate or derivatives thereof) or alternatively a mixture of a base (usually a weak base, e.g. histidine) and its conjugate acid (e.g. protonated histidine salt). The pH of a "buffer solution" will change only slightly upon addition of a small quantity of strong acid or base due to the "buffering effect" imparted by the "buffering agent".

Herein, a "buffer system" comprises one or more buffering agent(s) and/or an acid/base conjugate(s) thereof, and more suitably comprises one or more buffering agent(s) and an acid/base conjugate(s) thereof. Unless stated otherwise, any concentrations stipulated herein in relation to a "buffer system" (i.e. a buffer concentration) suitably refers to the combined concentration of the buffering agent(s) and/or acid/base conjugate(s) thereof. In other words, concentrations stipulated herein in relation to a "buffer system" suitably refer to the combined concentration of all the relevant buffering species (i.e. the species in dynamic equilibrium with one another, e.g. phosphate(s)/phosphoric acid(s)). As such, a given concentration of a phosphate and/or a histidine buffer system generally relates to the combined concentration of histidine and the imidazolium form of histidine and/or phosphate(s) and/or phosphoric acid(s). In the case of phosphate buffer systems, such concentrations are usually straightforward to calculate by reference to the input quantities of phosphate salts (including any hydrogen phosphate salts, e.g. monohydrogen phosphate, dihydrogen phosphate, and/or trihydrogen phosphate). In the case of histidine, such concentrations are usually straightforward to calculate by reference to the input quantities of histidine or a salt thereof. The overall pH of the composition comprising the relevant buffer system is generally a reflection of the equilibrium concentration of each of the relevant buffering species (i.e. the balance of buffering agent(s) to acid/base conjugate(s) thereof).

Herein, the term "buffering agent" refers to an acid or base component (usually a weak acid or weak base) of a buffer or buffer solution. A buffering agent helps maintain the pH of a given solution at or near to a pre-determined value, and the buffering agents are generally chosen to complement the pre-determined value. A buffering agent is suitably a single compound which gives rise to a desired buffering effect, especially when said buffering agent is mixed with (and suitably capable of proton exchange with) an appropriate amount (depending on the pre-determined pH desired) of its corresponding "acid/base conjugate", or if the required amount of its corresponding "acid/base conjugate" is formed in situ—this may be achieved by adding strong acid or base until the required pH is reached. By way of example:

A phosphate "buffering agent" is suitably a phosphate salt, for example, a sodium phosphate (which may include one or a mixture of two or more phosphates, such as a mixture of monosodium phosphate, disodium phosphate monobasic, and/or trisodium phosphate) suitably mixed with its acid/base conjugate, phosphoric acid. Such a buffer system may be formed by simply mixing a given amount of phosphate salt(s) with a given amount of phosphoric acid. Alternatively, however, such a buffer may be formed by adding a given amount of a base, suitably a strong base (e.g. sodium hydroxide) to the phosphoric acid until the desired pH (and thus the desired balance of sodium acetate/acetic acid) is reached. Herein, except where the contrary is stated, any concentrations given in relation to a phosphate buffer or phosphate buffering agent suitably refer to the combined concentration of the buffering agent(s) (e.g. sodium phosphate(s)) and/or acid/base conjugate(s) thereof (e.g. phosphoric acid). The skilled person is readily able to calculate such concentrations. Such concentrations may be calculated by reference to the combined concentrations of buffering agent(s) and acid/base conjugate(s), where a buffer system is formed by simply mixing together buffering agent(s) and acid/base conjugate(s). Alternatively, where a buffer system is formed by mixing either the buffering agent(s) or acid/base conjugate(s) with a pH adjuster (e.g. strong acid or strong base) to produce a mixture of each, suitably such concentrations may be calculated by reference to the starting amounts/concentrations of the buffering agent(s) or acid/base conjugate(s) respectively. For example, where a buffer system is formed using a known amount/concentration of phosphoric acid which is mixed with a pH adjuster (e.g. sodium hydroxide) until the desired pH is reached, the concentration of the buffer system may be calculated by reference to the initial amount of phosphoric acid.

A citrate "buffering agent" is suitably a citrate salt, for example, sodium citrate, suitably mixed with its acid/base conjugate, citric acid. Such a "buffer system" may be formed by simply mixing a given amount of sodium citrate with a given amount of citrate acid. Alternatively, however, such a buffer may be formed by adding a given amount of a base, suitably a strong base (e.g. sodium hydroxide) to the citric acid until the desired pH (and thus the desired balance of sodium citrate/citric acid) is reached. Herein, except where the contrary is stated, any concentrations given in relation to a citrate buffer or citrate buffering agent suitably refer to the combined concentration of the buffering agent(s) (e.g. sodium citrate) and/or acid/base conjugate(s) thereof (e.g. citric acid). The skilled person is readily able to calculate such concentration. Such concentrations may be calculated by reference to the combined concentrations of buffering agent(s) and acid/base conjugate(s), where a buffer system is formed by simply mixing together buffering agent(s) and acid/base conjugate(s). Alternatively, where a buffer system is formed by mixing either the buffering agent(s) or acid/base conjugate(s) with a pH adjuster (e.g. strong acid or strong base) to produce a mixture of each, suitably such concentrations may be calculated by reference to the starting amounts/concentrations of the buffering agent(s) or acid/base conjugate(s) respectively. For example, where a buffer system is formed using a known amount/concentration of citric acid which is mixed with a pH adjuster (e.g. sodium hydroxide) until the desired pH is reached, the concentration of the buffer system may be calculated by reference to the initial amount of citric acid.

Herein, an "acid/base conjugate" refers to the conjugate acid or conjugate base (whichever is relevant at a particular pH—typically the conjugate acid in the context of the present invention) of a particular "buffering agent". The acid/base conjugate of a phosphate buffering agent (e.g. sodium phosphate) is suitably phosphoric acid (though this may suitably include higher hydrogen phosphate salts, such as mono- or di-hydrogen phosphates, which are potentially conjugate acids to phosphate or lower hydrogen phosphate salts thereof). The acid/base conjugate of a citrate buffering agent (e.g. sodium citrate) is suitably citric acid.

Herein, the term "buffering species" refers to the particular species (excluding any associated counteranions or countercations—i.e. ignore sodium counterions for phosphate(s)/phosphoric acid(s) systems, and ignore chloride or hydroxide counter-ions for histidine/imidazolium-histidine systems) of a given buffer system which are in dynamic equilibrium with (and proton-exchange with) one another. For example, phosphate, monohydrogenphosphate, and dihydrogenphosphate anions and phosphoric acid may together constitute "phosphate buffering species" of a "phosphate buffer system" (though depending on the pH, some may be more prevalent than others within the buffer system). For example, citrate anions and citric acid together constitute a "citrate buffering species" of a "citrate buffer system".

Since it is often somewhat difficult to define quantities (whether absolute or relative) of a buffer system by reference to weight (since the total weight will depend on the desired pH, which will affect the amount of counterions present), herein weight-based quantities may instead be determined by reference to a theoretical weight of a relevant or arbitrary "buffering species". At least two species are generally present in any given set of "buffering species" (in relative amounts that can only be determined by reference to the pH), each with a different molecular weight (which usually differs by just 1, though for phosphate buffers multiple phosphate species may be present). Therefore, to enable viable weight calculations and references, for the purposes of this specification the weight of any given set of "buffering species" is given as a theoretical weight based on just one of the buffering species. Depending on the buffer system in question, this may conveniently be the most acidic of the buffering species (i.e. the most protonated form at any given pH) or the most basic of the buffering species (i.e. the least protonated form at any given pH), or may simply be one of the buffering species. By way of example, in a phosphate system the phosphate buffering species may consist of phosphate anions (ignore countercations) and phosphoric acid (and/or one or more corresponding hydrogenphosphates). The weight of the "buffering species" may therefore be calculated as if phosphoric acid was the only species present in the buffer system (even though phosphate species are clearly present alongside phosphoric acid, and even if only minimal phosphoric acid is actually present at the given pH). Thus, any reference to a weight or weight ratio involving a "phosphatebuffering species" suitably refers to the theoretical weight of phosphoric acid equivalents within the buffer system. As such, where a composition is formed by adding a pH adjuster (e.g. sodium hydroxide) to a fixed amount of phosphoric acid, the original weight of phosphoric acid may be considered to be the weight of the "buffering species" regardless of the ultimate pH. Alternatively, if the concentration (i.e. molarity) of a buffer system is known (or if the relevant buffering system is formed by adding an acidic pH adjust, such as phosphoric acid, to a fixed amount of phosphate species), this can be converted into a weight of "buffering species" by reference to the molecular weight of the most acidic form of the relevant buffering species (e.g. phosphoric acid), and ignoring the fact that phosphate anions are also present. A similar principle applies to citric acid for citrate buffer systems.

It will be understood by those skilled in the art that many buffering species may adopt a variety of different forms. Furthermore, acids, such as phosphoric acid, may in themselves adopt a variety of forms—collectively "phosphoric acids"—and the present invention suitably includes any of these forms.

Unless stated otherwise, references herein to an "amino acid" or "amino acids", whether specific (e.g. arginine, histidine) or general (e.g. any amino acid), in the context of their presence or otherwise within compositions (especially pharmaceutical liquid compositions of the invention) relate to the corresponding free amino acid(s) (regardless of its/their protonation state and/or salt form, though for consistency amounts are suitably calculated by reference to the free amino acid per se). This may suitably include natural and/or artificial amino acids. Unless stated to the contrary, such references are not intended to relate to amino acid residue(s) covalently incorporated as part of a larger compound (as opposed to a composition comprising multiple compounds), such as a peptide or protein (where such amino acid residues are linked via peptide bonds). As such, though etanercept, as a protein, contains amino acid residues, it is not considered to comprise any "free amino acid(s)". By way of example, a composition defined as being "free of arginine" does not contain any free arginine but it may still include one or more proteins (e.g. etanercept) which do themselves comprise arginine residues.

Unless stated otherwise, references herein to any one or more "amino acids", whether specific or general, suitably relate to the L-stereoisomers or at least to a mixture comprising the L-stereoisomers. Most suitably such "amino acids" are L-amino acids.

The term "substantially free", when used in relation to a given component of a composition (e.g. "a liquid pharmaceutical composition substantially free of arginine"), refers to a composition to which essentially none of said component has been added. As explained above, such references have no bearing on the presence of amino acid residue(s) within a protein structure. When a composition is "substantially free" of a given component, said composition suitably comprises no more than 1.0 wt % of said component, suitably no more than 0.1 wt % of said component, suitably no more than 0.01 wt % of said component, suitably no more than 0.001 wt % of said component, suitably no more than 0.0001 wt % of said component, suitably no more than 0.00001 wt %, suitably no more than 0.000001 wt %, suitably no more than 0.0000001 wt % thereof, most suitably no more than 0.0001 parts per billion (by weight).

The term "entirely free", when used in relation to a given component of a composition (e.g. "a liquid pharmaceutical composition substantially free of arginine"), refers to a composition containing none of said component. As explained above, such references have no bearing on the presence of amino acid residue(s) within a protein structure.

Herein, in the context of the present specification, a "strong acid" is suitably one having a $pK_a$ of −1.0 or less, whereas a "weak acid" is suitably one having a $pK_a$ of 2.0 or more. Herein, in the context of the present specification, a "strong base" is suitably one whose conjugate acid has a $pK_a$ of 12 or higher (suitably 14 or higher), whereas a "weak base" is suitably one whose conjugate acid has a $pK_a$ of 10 or less.

Herein, a "stabiliser" refers to a component which facilitates maintenance of the structural integrity of the biopharmaceutical drug, particularly during freezing and/or lyophilization and/or storage (especially when exposed to stress). This stabilising effect may arise for a variety of reasons, though typically such stabilisers may act as osmolytes which mitigate against protein denaturation. Typical stabilisers include sugar stabilisers, such as a sugar polyol (e.g. mannitol, sorbitol), and/or a disaccharide (e.g. trehalose, sucrose, maltose, lactose), though the liquid pharmaceutical compositions of the invention include a stabiliser, at least one of which is a sugar stabiliser (i.e. either a sugar polyol or a disaccharide).

Herein, a "tonicity modifier" or "tonicifier" refers to a reagent whose inclusion within a composition suitably contributes to (or increases) the overall osmolality and osmolarity of the composition. Suitably, a tonicifier, as used herein includes an agent which functions to render a solution similar in osmotic characteristics to physiologic fluids.

Herein, references to specific amounts of a given component of a composition, especially a buffering agent (or buffer system), stabiliser, amino acid, surfactant, or tonicifier, suitably relate to the amounts of the pure anhydrous form of the relevant component (or compositions formed by using said amounts of the pure anhydrous form), even though such a component may be used in a non-anhydrous form when forming the composition. Amounts of any corresponding non-anhydrous forms (e.g. monohydrates, dihydrates, etc.) may be readily calculated by simply using the appropriate multiplier.

Herein, references to any given component of a composition, unless stated otherwise, suitably includes alternative forms of said component or includes said component where it is formed from alternative forms, such as any salt, free base, free acid, solvate, or complex thereof, especially in respect of a buffering agent (or buffer system), stabiliser, amino acid, surfactant, or tonicifier. As such, reference to a composition comprising a given compound (e.g. arginine) includes any equivalent compositions comprising said component in an alternative form (e.g. arginine hydrochloride), or any equivalent composition formed by the incorporation of an alternative form of arginine (e.g. arginine hydrochloride). However, unless stated otherwise, any amounts stipulated in respect of the given component (especially when given in terms of weight or weight concentration/proportion) will suitably relate to the amount of the stipulated form of said component, not the amount of any alternative form thereof (e.g. salt). A conversion factor will need to be applied to establish the equivalent amount of said component in any alternative form, such as salt, free base, free acid, solvate, or complex thereof—this may be calculated by the skilled person, simply by reference to relevant molecular weights of the relevant species. As such, wherever the invention is defined by reference to a stipulated amount of "arginine", this covers compositions containing that amount of arginine in zwietterionic form, even if the source of arginine is an alternative form, and even if the arginine exists within the composition in an alternative form (e.g. which may well depend on pH).

Herein, the term "pharmaceutical composition" refers to a formulation of a pharmaceutical active which renders the biological activity of the active ingredient therapeutically effective, but which does not include other ingredients which are obviously toxic to a subject to which the formulation are intended to be administered.

Herein, the term "stable" generally refers to the physical stability and/or chemical stability and/or biological stability of a component, typically a pharmaceutical active or composition thereof, during preservation/storage.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

In the context of the present invention, a "therapeutically effective amount" or "effective amount" of the etanercept means an amount that is effective, when administered to a mammal for treating a disease or disorder, in prophylactic and therapeutic aspect and the antibody is effective in treatment of the diseases concerned.

The "therapeutically effective amount" will vary depending on the compound, the disease and its severity and the age, weight, etc., of the mammal to be treated.

The term "human TNF-α" refers to the human cytokine which exists in a 17 kD secreted form and a 26 kD membrane-associated form, and in a biologically active form, TNF-α could be observed as a trimer of covalently-bound 17 kD molecule. Its specific structure can be found in Pennica, D. et al. (1984) Nature 312: 724-729; Davis, J. M. et al. (1987) Biochemistry 26, 1322-1326; and Jones, E. Y. et al. (1989) Nature 338: 225-228.

Herein, amounts stipulated for components and ingredients, whether specified in terms of "parts", ppm (parts per million), percentages (%, e.g. wt %), or ratios, are intended to be by weight, unless stated otherwise.

Where the quantity or concentration of a particular component of a given composition is specified as a weight percentage (wt % or % w/w), said weight percentage refers to the percentage of said component by weight relative to the total weight of the composition as a whole. It will be understood by those skilled in the art that the sum of weight percentages of all components of a composition (whether or not specified) will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essential but suitable additives).

Herein, unless stated otherwise, the term "parts" (e.g. parts by weight, pbw) when used in relation to multiple ingredients/components, refers to relative ratios between said multiple ingredients/components. Expressing molar or weight ratios of two, three or more components gives rise to the same effect (e.g. a molar ratio of x, y, and z is $x_1:y_1:z_1$ respectively, or a range $x_1-x_2:y_1-y_2:z_1-z_2$). Though in many embodiments the amounts of individual components within a composition may be given as a "wt %" value, in alternative embodiments any or all such wt % values may be converted to parts by weight (or relative ratios) to define a multi-component composition. This is so because the relative ratios between components is often more important than the absolute concentrations thereof in the liquid pharmaceutical compositions of the invention. Where a composition comprising multiple ingredients is described in terms of parts by weight alone (i.e. to indicate only relative ratios of ingredients), it is not necessary to stipulate the absolute amounts or concentrations of said ingredients (whether in toto or individually) because the advantages of the invention can stem from the relative ratios of the respective ingredients rather than their absolute quantities or concentrations. However, in certain embodiments, such compositions consists essentially of or consist of the stipulated ingredients and a diluents (e.g. water).

Where a composition is said to comprise a plurality of stipulated ingredients (optionally in stipulated amounts of concentrations), said composition may optionally include additional ingredients other than those stipulated. However, in certain embodiments, a composition said to comprise a plurality of stipulated ingredients may in fact consist essentially of or consist of all the stipulated ingredients.

Herein, where a composition is said to "consists essentially of" a particular component, said composition suitably comprises at least 85 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

Herein, the term "particle size" or "pore size" refers respectively to the length of the longest dimension of a given particle or pore. Both sizes may be measured using a laser particle size analyser and/or electron microscopes (e.g. tunneling electron microscope, TEM, or scanning electron microscope, SEM). The particle count (for any given size) can be obtained using the protocols and equipment outlined in the Examples, which relates to the particle count of sub-visible particles.

Herein, unless stated otherwise, all chemical nomenclature may be defined in accordance with IUPAC definitions.

Liquid Pharmaceutical Composition

The present invention provides a liquid pharmaceutical composition, suitably as defined herein. The composition suitably comprises a protein, suitably one which inhibits human TNF-α activity, suitably so as to prevent it from activating TNF receptors. Suitably the liquid pharmaceutical composition comprises a fusion protein, suitably a fusion protein comprising a TNF receptor linked to an Fc portion of an IgG1. Most suitably, the pharmaceutical composition comprises etanercept, including any biosimilar thereof.

The composition suitably comprises a buffer system or a buffering agent. The composition suitably comprises a buffer system, and the pH of the composition is suitably between pH 5.7 and 6.9. Suitably the buffer system maintains the composition at a (substantially) constant pH (suitably varying by no more than +1-0.5 pH units, suitably by no more than +1-0.2 pH units, suitably by no more than +1-0.1 pH units under standard storage and use conditions).

The composition suitably comprises a tonicifier. Suitably the tonicifier serves to provide the composition with an osmolality or tonicity close to that of or (substantially) isotonic with body fluids.

The composition suitably comprises a stabiliser, suitably a sugar stabiliser.

The composition is suitably (substantially or entirely) free of arginine or comprises arginine either in a concentration of at most 0.1 mM, or in a weight ratio of arginine to etanercept of at most 1:3000 (i.e. less than or equal to one part by weight of arginine for every 3000 parts by weight etanercept). Alternatively or in addition, the composition may suitably include any one or more additional components defined herein in relation to a liquid pharmaceutical composition (e.g. including particular amino acid(s), excluding particular amino acid(s)), optionally in any amount, concentration, or form stipulated herein; and wherein the composition optionally exhibits any one or more parameters or properties given herein in relation to a liquid pharmaceutical composition (e.g. pH).

Advantageously, the present invention provides alternative and improved liquid pharmaceutical compositions, which generally exhibit better stability and viability than those of the prior art. As is illustrated herein (see Examples), the liquid pharmaceutical formulations of the present invention have comparable or even improved characteristics when compared to the conventional formulations of etanercept, for example the commercially available formulation Enbrel®, when subjected to different stressing conditions (thermal, mechanical and light). Since most preferably the compositions of the invention are (substantially) arginine-free, they offer significant benefits associated with the avoidance of arginine-specific side effects. That such good stability performance can be achieved using less complex formulations, with fewer excipients, and generally without arginine, was considered surprising in view of the general teachings of the prior art.

Etanercept

As detailed in the definitions section, references herein to "etanercept" include the originator drug substance (commercially available as Enbrel®), as well as etanercept as defined in WO91/03553 and WO 9406476 and U.S. Pat. No. 5,605, 690 (all Immunex) and elsewhere in the art, and also biosimilars thereof.

Furthermore, references herein to "etanercept" may include biosimilars, such as those defined in the definitions section. The skilled person would readily appreciate the scope of the term "etanercept" in the context of the invention.

Etanercept used in compositions of the invention is suitably substantially purified.

Herein, etanercept employed in the compositions and methods of the invention are suitably "substantially purified", suitably containing at least 90% by weight, more suitably at least 95% by weight, of the relevant polypeptide, wherein the weight of the polypeptide includes any carbohydrate, lipid, or other residues covalently attached to the polypeptide, notwithstanding some tolerable variation in the extent and type of glycosylation or other post-translation modification, or with respect to conformation or extent of multimerization.

The medical indications and function of etanercept, are elucidated hereinbefore.

In an embodiment, the liquid pharmaceutical composition comprises etanercept at a concentration of from about 5 to about 150 mg/ml, suitably from about 20 to about 70 mg/mL, suitably from about 15 to 35 mg/mL or from about 40 to 60 mg/mL. In an embodiment, the etanercept is present at a concentration from about 20 to about 30 mg/ml—most suitably at a concentration of about 25 mg/ml. In an embodiment, the etanercept is present at a concentration from about 45 to about 55 mg/ml-most suitably at a concentration of about 50 mg/ml.

Buffer Systems and pH

Suitably, the liquid pharmaceutical composition is a buffered solution. The pH of the buffered solution is suitably stabilised by a buffering agent (or a buffer system), suitably in combination with an acid/base conjugate of the buffering agent. As such, the liquid pharmaceutical composition suitably comprises a buffering agent (or at least one buffering agent) as defined herein. Preferably, the liquid pharmaceutical composition additionally comprises an acid/base conjugate, wherein said acid/base conjugate corresponds to the conjugate acid or conjugate base of the buffering agent, depending on whether the buffering agent is itself a base or acid respectively. Collectively, the buffering agent and its acid/base conjugate (which may be plural in some cases, such as phosphate buffer systems which comprise numerous buffering species) may be considered a "buffer system". The liquid pharmaceutical composition thus suitably comprises a "buffer system" (suitably comprising a buffering agent(s) and an acid/base conjugate(s) thereof), and any concentrations stipulated in relation to the buffer system generally relate to the combined concentrations of the buffering agent(s) and any acid/base conjugate(s) thereof. Any "buffer system" suitably comprises a weak acid and a weak base (see above definitions).

Suitably, the buffer system is a phosphate buffer system and/or a citrate buffer system. Suitably, the liquid pharmaceutical composition comprises at most one buffer system, which is most suitably a phosphate buffer system or a citrate buffer system.

Suitably, the buffering agent is a phosphate buffering agent. Suitably the phosphate buffering agent is a phosphate (or hydrogenphosphate salt), suitably comprising anionic phosphate species and one or more pharmaceutically acceptable countercations. A suitable phosphate salt may include a metal phosphate salt (e.g. an alkali metal phosphate or an alkaline earth metal phosphate, which may include one or more of the various hydrogen phosphates), or a non-metal phosphate salt (e.g. ammonium phosphate, triethylammonium phosphate, which may include one or more of the various hydrogen phosphates). In a particular embodiment, the buffering agent (and the phosphate salt) comprises sodium phosphate(s) (which may include sodium hydrogen phosphate and/or sodium dihydrogen phosphate as well as optionally including trisodium phosphate).

Suitably, the liquid pharmaceutical composition comprises an acid/base conjugate(s) of the buffering agent(s), most suitably phosphoric acid (or a hydrogen phosphate) as the conjugate acid of a phosphate salt. The combination of the buffering agent(s) and its acid/base conjugate(s) constitute a buffer system. Suitably, the liquid pharmaceutical composition comprises the buffering agent(s) and its corresponding acid/base conjugate(s), suitably such that together the buffering agent(s) and its acid/base conjugate(s) are present at a level (i.e. absolute amount or concentration) and in a relative amount (or concentration) sufficient to provide the desired pH for the composition. The buffer system may be formed in a variety of ways, especially where phosphate buffer systems are concerned, where multiple buffering species may be present. The buffer system may be formed by simply mixing the buffering agent(s) with its acid/base conjugate(s) or may alternatively be formed by mixing an acid or base with either the buffering agent(s) or its acid/base conjugate(s) in order to form in situ the desired mixture of buffering agent(s) and acid/base conjugate(s). For example, the buffer system may be formed by simply mixing a phosphate buffering agent (e.g. sodium phosphate and/or related hydrogen phosphate(s)) with its acid/base conjugate (i.e. phosphoric acid) or indeed with a strong acid (e.g. hydrochloric acid), suitably in a ratio appropriate to furnish the desired pH. Alternatively, the buffer system may be formed by adding a base (e.g. sodium hydroxide) to the acid/base conjugate (i.e. phosphoric acid and/or related hydrogen phosphate(s)) of the phosphate buffering agent, suitably in an amount appropriate to furnish the desired pH and mixture of the buffering agent (e.g. sodium phosphate(s)) and corresponding acid/base conjugate(s) (i.e. phosphoric acid). Alternatively, either method of forming the buffer system may be employed, and pH may be judiciously adjusted by either adding further acid (suitably strong acid, such as HCl) or further base (suitably strong base, such as sodium hydroxide).

Most suitably, the buffer system is or at least comprises a phosphate buffer system, suitably comprising a mixture of one or more phosphate salts (suitably selected from tribasic phosphate salts, dibasic hydrogen phosphate salts, or monobasic dihydrogen phosphate salts) and/or phosphoric acid.

In some embodiments, the buffer system comprises two or more buffer systems, for example a phosphate buffer system and another buffer system, such as a citrate or histidine buffer system. In respect of the phosphate buffer system, the buffering agent and buffering species may be as described above. A citrate and/or a histidine buffer system may be formed following the same or similar principles as per the phosphate buffer system.

Suitably, the liquid pharmaceutical composition has a pH greater than or equal to pH 5.5, more suitably greater than or equal to pH 5.8, most suitably greater than or equal to pH 6.2.

Suitably, the liquid pharmaceutical composition has a pH less than or equal to pH 7.0, more suitably less than or equal to pH 6.8, most suitably less than or equal to pH 6.4.

Suitably, liquid pharmaceutical composition has a pH between pH 6.1 and 6.5. More suitably, the liquid pharmaceutical composition has a pH between pH 6.2 and 6.4, most suitably a pH of 6.3 (optionally+/−0.2).

Within these pH ranges, the predominant buffering species present within a phosphate buffer system are monohydrogen phosphate and dihydrogen phosphate.

Within these pH ranges, the predominant buffering species present within a citrate buffer system are monohydrogen citrate (i.e. citrate dianion) and citrate (i.e. citrate trianion).

Suitably, the liquid pharmaceutical composition comprises a buffer system (suitably a phosphate buffer system, suitably comprising a phosphate buffering agent; or a citrate buffer system, suitably comprising a citrate buffering agent) at a concentration of from about 1 to 50 mM, more suitably from about 10 to 40 mM, most suitably from about 20 mM to 30 mM. In a particular embodiment, the liquid pharmaceutical composition comprises a buffer system at a concentration of about 25 mM.

In an embodiment, the liquid pharmaceutical composition comprises a phosphate buffer system comprising two or more buffering species selected from phosphoric acid, dihydrogenphosphate, monohydrogenphosphate, and phosphate (and/or derivatives thereof—e.g. o-phosphoric acid), suitably with sodium counterions to any phosphate species, at a collective concentration of from about 1 to 50 mM, suitably from about 10 to 40 mM, more suitably from about 20 mM to 30 mM, most suitably at a collective concentration of about 25 mM.

In an embodiment, the liquid pharmaceutical composition comprises a citrate buffer system comprising two or more buffering species, suitably selected from citrate acid, dihydrogen citrate, monohydrogen citrate, and citrate (and/or derivatives thereof), suitably with sodium counterions to any citrate species, at a collective concentration of from about 1 to 50 mM, suitably from about 10 to 40 mM, more suitably from about 20 mM to 30 mM, most suitably at a collective concentration of about 25 mM.

In an embodiment, where more than one buffer system is present (e.g. a citrate buffer system as well as a phosphate buffer system) the sum of the individual concentrations of each of the respective buffer systems (i.e. the collective concentration) may suitably fall within any one of the aforementioned buffer system concentrations.

Suitably, the liquid pharmaceutical composition comprises a phosphate buffer system wherein the phosphate buffering species are present within the composition at a concentration (defined by reference to phosphoric acid equivalents, i.e. hypothetically assuming all of the buffering species are in the phosphoric acid form, MW=98) of from about 2.45 μg/mL to 24.5 mg/mL (i.e. 2.45 μg/mL to 24.5 mg/mL of phosphoric acid equivalents), suitably from about 0.245 mg/mL to about 12.25 mg/mL, suitably from about 1.225 mg/mL to about 3.675 mg/mL, most suitably about 2.45 mg/mL.

Suitably, the weight ratio of phosphate buffering species (in terms of phosphoric acid equivalents) to etanercept within the liquid pharmaceutical composition is between 1:200 and 1:2, suitably between 1:100 and 1:4, suitably between 1:50 and 1:10, suitably about 1:20.4.

Suitably, the liquid pharmaceutical composition comprises a citrate buffer system wherein the citrate buffering species are present within the composition at a concentration (defined by reference to citric acid equivalents, i.e. hypothetically assuming all of the buffering species are in the citric acid form, MW=192.12 g mol$^{-1}$) of from about 4.8 μg/mL to 48 mg/mL (i.e. 4.8 μg/mL to 48 mg/mL of citric acid equivalents), suitably from about 0.48 mg/mL to about 24 mg/mL, suitably from about 2.4 mg/mL to about 7.2 mg/mL, most suitably about 4.8 mg/mL.

Suitably, the weight ratio of citrate buffering species (in terms of citric acid equivalents) to etanercept within the liquid pharmaceutical composition is between 1:100 and 1:1, suitably between 1:50 and 1:2, suitably between 1:25 and 1:5, suitably about 1:10.

Suitably, the liquid pharmaceutical composition comprises the buffer system (suitably a phosphate and/or citrate buffer system) in a molar ratio of buffer system (in terms of moles of buffering species) to etanercept of from about 5:1 to about 100:1. In an embodiment, the buffer system is present in a molar ratio of buffer system to etanercept of from about 10:1 to about 50:1, most suitably about 25:1. This includes where the "buffering agent(s)" (e.g. sodium citrate) is formed by the addition of a strong base (e.g. sodium hydroxide) to the conjugate acid of the buffering agent (e.g. citric acid).

As illustrated in the Example section, liquid pharmaceutical compositions of the invention including an acetate buffer system perform particularly well in stress tests, thus validating the stability and drug product viability of the compositions of the invention.

Tonicifier

The liquid pharmaceutical composition of the invention suitably comprises a "tonicity modifier" (or "tonicifier") or one or more tonicifiers, suitably as defined herein.

The inclusion of a tonicifier suitably contributes to (or increases) the overall osmolality and osmolarity of the composition. Suitably a tonicifier is present within the composition in a quantity or concentration sufficient for the composition to be (substantially) isotonic with body fluids. However, the tonicifier (suitably in combination with the stabiliser) is also potentially important in the stabilisation of etanercept.

Any suitable tonicifier may be used. However, suitably the tonicifier is selected from the group including water-soluble metal salts (e.g. sodium chloride, potassium chloride, magnesium chloride, calcium chloride), water-soluble tonicifying sugars/sugar alcohols (albeit different from any components serving as a stabiliser), and/or other water-soluble polyols. Suitably the tonicifier(s) is non-buffering (i.e. gives rise to little or no buffering effect). As such, any metal salt tonicifiers are suitably not buffering agents.

The liquid pharmaceutical composition may comprise one or more tonicifiers, though preferably only a single "tonicifier" is present (notwithstanding any tonicifying effects imparted to the composition by components intended to serve another function as defined herein, such as a stabiliser).

Most preferably, the tonicifier is or comprises a metal salt (preferably a non-buffering water-soluble metal salt). Suitably, said metal salt is or comprises a metal halide, suitably an alkali or an alkaline earth metal halide, suitably an alkali metal chloride.

In a particular embodiment, the tonicifier is or comprises sodium chloride. In a particular embodiment, the tonicifier is sodium chloride. Sodium chloride is a particularly advantageous tonicifier for use alongside a sucrose or trehalose stabiliser, especially with a phosphate or citrate buffer system.

Suitably, the liquid pharmaceutical composition comprises the tonicifier(s) (most suitably sodium chloride) at a concentration of from about 10 to about 200 mM, more suitably from about 20 to about 150 mM, more suitably from about 25 to about 75 mM or from about 75 mM to about 125 mM. In an embodiment, the tonicifier(s) is present at a concentration of between 40 and 60 mM, most suitably about 50 mM. In an embodiment, sodium chloride is present at a concentration of 50 mM. In an embodiment, the tonicifier(s) is present at a concentration of between 90 and 110 mM, most suitably about 100 mM. In an embodiment, sodium chloride is present at a concentration of 100 mM.

Suitably, the liquid pharmaceutical composition comprises the tonicifier(s) (most suitably sodium chloride) at a concentration of from about 0.58 mg/mL to about 11.6 mg/mL, more suitably from about 1.16 mg/mL to about 8.76 mg/mL, more suitably from about 1.46 mg/mL to about 4.38 mg/mL or from about 4.38 mg/mL to about 7.3 mg/mL. In an embodiment, the tonicifier(s) is present at a concentration of between 2.34 mg/mL and 3.50 mg/mL, most suitably about 2.92 mg/mL. In an embodiment, sodium chloride is present at a concentration of 2.92 mg/mL. In an embodiment, the tonicifier(s) is present at a concentration of between 5.26 mg/mL and 6.42 mg/mL, most suitably about 5.84 mg/mL. In an embodiment, sodium chloride is present at a concentration of 5.84 mg/mL.

Suitably, the liquid pharmaceutical composition comprises the tonicifier(s) (most suitably sodium chloride) in a molar ratio of tonicifier to etanercept of from about 10:1 to about 200:1, more suitably from about 20:1 to about 150:1, more suitably from about 25:1 to about 75:1 or from about 75:1 to about 125:1. In an embodiment, the tonicifier(s) is present at a molar ratio of tonicifier to etanercept of from about 40:1 to about 60:1, most suitably about 50:1. In an embodiment, sodium chloride is present at a molar ratio of sodium chloride to etanercept of about 50:1. In an embodiment, the tonicifier(s) is present at a molar ratio of tonicifier to etanercept of from about 90:1 to about 110:1, most suitably about 100:1. In an embodiment, sodium chloride is present at a molar ratio of sodium chloride to etanercept of about 100:1

As illustrated in the Example section, liquid pharmaceutical compositions of the invention including a tonicifier as defined herein perform particularly well in stress tests, with compositions comprising sodium chloride in an amount range as stipulated performing particularly well.

Stabiliser

Suitably, the liquid pharmaceutical composition comprises a stabiliser, most suitably a sugar stabiliser. Suitably, such a component facilitates maintenance of the structural integrity of the biopharmaceutical drug, particularly during freezing and/or lyophilization and/or storage (especially when exposed to stress).

The liquid pharmaceutical composition may comprise one or more sugar stabilisers, though in preferred embodiments only a single sugar stabiliser is present.

Suitably, the sugar stabiliser is a disaccharide.

The sugar stabiliser is/are sucrose and/or trehalose.

In a particular embodiment, the sugar stabiliser is sucrose.

Suitably, the liquid pharmaceutical composition comprises at most one sugar stabiliser, suitably at most one sugar polyol and/or disaccharide. Suitably, the liquid pharmaceutical composition comprises sucrose as the only sugar stabiliser.

Suitably the sucrose used to form the liquid pharmaceutical composition is anhydrous sucrose. Regardless of the hydration state used, any amounts stipulated in relation to sucrose (unless stated otherwise) pertain to pure, anhydrous sucrose. Such amounts may be converted into an amount of sucrose hydrate by applying an appropriate multiplier. Moreover, for the purposes of assessing whether a given formulation falls within the scope of any of the sucrose quantity definitions given herein, an amount of sucrose hydrate can be readily converted into a corresponding amount of pure, anhydrous sucrose (with an equal number of moles) through applying said multiplier in reverse. This principle may be adopted for any sugar stabiliser component. Concentrations, when given as a molar concentration, will of course be the same regardless of the hydration state of the sugar stabiliser.

Suitably, the liquid pharmaceutical composition comprises the sugar stabilizer(s) (most suitably sucrose) at a weight concentration of from about 0.1 to about 10 wt %, more suitably from about 0.5 to about 5 wt %, more suitably from about 0.75 to about 1.25 wt % or from about 3.5 to about 4.5 wt %. In an embodiment, the sugar stabilizer(s) is present at a weight concentration of about 1 wt %. In an embodiment, sugar stabilizer(s) is present at a weight concentration of about 4 wt %.

Suitably, the liquid pharmaceutical composition comprises the sugar stabilizer(s) (most suitably sucrose) at a concentration of from about 5 to about 200 mM, more suitably from about 10 to about 150 mM, more suitably from about 20 to about 40 mM or from about 110 to about 130 mM. In an embodiment, the sugar stabilizer(s) is present at a concentration of about 30 mM. In an embodiment, the sugar stabilizer(s) is present at a concentration of 120 mM.

Suitably, the liquid pharmaceutical composition comprises the sugar stabilizer(s) (most suitably sucrose) at a concentration of from about 1 mg/mL to about 100 mg/mL, more suitably from about 5 mg/mL to about 50 mg/mL, more suitably from about 7.5 mg/mL to about 12.5 mg/mL or from about 35 mg/mL to about 45 mg/mL. In an embodiment, the sugar stabilizer(s) is present at a concentration of about 10 mg/mL. In a particular embodiment, the sugar stabilizer(s) is present at a concentration of about 40 mg/mL.

Suitably, the liquid pharmaceutical composition comprises the sugar stabilizer(s) (most suitably sucrose) in a molar ratio of sugar stabilizer(s) to etanercept of from about 10:1 to about 200:1, more suitably from about 20:1 to about 150:1, more suitably from about 25:1 to about 125:1. In an embodiment, the sugar stabilizer(s) is present at a molar ratio of sugar stabilizer(s) to etanercept of from about 20:1 to about 40:1 or from about 110:1 to about 130:1. In an embodiment, sugar stabilizer(s) is present at a molar ratio of sugar stabilizer(s) to etanercept of about 30:1. In an embodiment, sugar stabilizer(s) is present at a molar ratio of sugar stabilizer(s) to etanercept of about 120:1.

As illustrated in the Example section, liquid pharmaceutical compositions of the invention including a sugar stabiliser as defined herein perform particularly well in stress tests. Furthermore, liquid pharmaceutical compositions comprising sucrose as the sugar stabiliser perform particularly well.

Polar Ionisable Amino Acids (and Optional Additional Amino Acids)

The liquid pharmaceutical composition suitably comprises a polar ionisable amino acid, suitably excluding arginine (and suitably also excluding any sulphur-containing amino acids). The polar ionisable amino acid is suitably a natural amino acid. The polar ionisable amino acid is both a polar (or hydrophilic) amino acid and an ionisable (or charged) amino acid. Such categorisations of amino acids are well known in the art. The term "polar amino acid" refers to amino acids bearing a polar side chain, whilst the term "Ionisable amino acid" refers to amino acids bearing a side chain that is or is capable of ionisation (e.g. protonation or deprotonation). Therefore, ionisable amino acids are either acidic amino acids or basic amino acids.

For the purposes of the present disclosure, polar natural amino acids suitably include: arginine, asparagine, aspartic acid, glutamine, glutamic acid, histidine, lysine, serine, and threonine. Ionisable natural amino acids suitably include: aspartic acid, glutamic acid, histidine, cysteine, lysine, tyrosine and arginine. Therefore, polar ionisable natural amino acids include: aspartic acid and glutamic acid, which may be considered "acidic amino acids"; and histidine, lysine, and arginine, which may be considered "basic amino acids". Thus suitably the polar ionisable amino acid is selected from the group consisting of aspartic acid, glutamic acid, histidine, and lysine.

In a particular embodiment, the polar ionisable amino acid is selected from the group consisting of aspartic acid, histidine, and lysine.

Where the polar ionisable amino acid is a basic amino acid, especially one of the more strongly basic amino acids (i.e. where the $pK_a$ of the side chain's conjugate acid/protonated form is greater than or equal to 10.0—thus excluding histidine), the liquid pharmaceutical composition may suitably comprise an additional non-polar amino acid, suitably excluding arginine (and suitably also excluding any sulphur-containing amino acids). The non-polar amino acid is suitably a natural amino acid. The term "non-polar amino acid" refers to amino acids bearing a non-polar (or hydrophobic) side chain. For the purposes of the present disclosure, non-polar natural amino acids suitably include: alanine, cysteine, glycine, isoleucine, leucine, methionine, phenylalanine, proline, tryptophan, tyrosine and valine.

Suitably the non-polar amino acid is one whose α-amino group has a relatively high $pK_a$ value (i.e. with respect to the $pK_a$ of its conjugate acid/protonated form), suitably a $pK_a$ value that is similar to the $pK_a$ of the side chain of its accompanying basic amino acid. Suitably the $pK_a$ of the conjugate acid/protonated form of the α-amino group of the non-polar amino acid is greater than or equal to 10.0). In a particular embodiment the non-polar amino acid is proline.

Suitably, where the liquid pharmaceutical composition comprises both a polar ionisable amino acid and a non-polar amino acid (e.g. lysine and proline), any amounts, concentrations, or ratios stipulated herein in relation to the polar ionisable amino acid alone may represent total amounts, concentrations, or ratios of the polar ionisable amino acid and non-polar amino acid in combination. As such, a non-polar amino acid may be included so as to replace a portion of the polar ionisable amino acid. The combination of lysine and proline is especially viable in this respect, particularly in certain preferred ratios.

Where the liquid pharmaceutical composition comprises both a polar ionisable amino acid and a non-polar amino acid (e.g. lysine and proline), suitably the molar ratio of polar ionisable amino acid to non-polar amino acid is between 10:1 and 1:10, more suitably between 5:1 and 1:5, more suitably between 2:1 and 1:2, most suitably about 1:1 (suitably +/−10%). As such, in a particular embodiment, the liquid pharmaceutical composition comprises lysine and proline in one of the aforementioned molar ratios, most suitably 1:1, and suitably the total amounts, concentrations, or ratios (e.g. relative to another non-amino acid component) of the two amino acids combined are defined by the amounts, concentrations, or ratios stipulated herein in relation to the polar ionisable amino acid alone.

Suitably, therefore, the liquid pharmaceutical composition suitably comprises a polar ionisable amino acid selected from the group consisting of:
  aspartic acid;
  histidine; and
  lysine (optionally, and most suitably in combination with a non-polar amino acid, most suitably proline).

Suitably, wherever the liquid pharmaceutical composition comprises a polar ionisable basic amino acid with a side chain whose conjugate acid/protonated form has a $pK_a$ greater than or equal to 10, the liquid pharmaceutical composition additionally comprises a non-polar amino acid (suitably excluding any sulphur-containing amino acids). Suitably no further amino acids are present.

Suitably, wherever the liquid pharmaceutical composition comprises a polar ionisable amino acid with a side chain whose conjugate acid/protonated form has a $pK_a$ less than 10, the liquid pharmaceutical composition is (substantially or entirely) free of any non-polar amino acids, and is suitably (substantially or entirely) free of any other amino acids.

Suitably, the liquid pharmaceutical composition suitably comprises either:
  aspartic acid;
  histidine; or
  a combination of lysine and proline;

suitably in an amount, concentration, or ratio (e.g. relative to another non-amino acid component) defined by any of the amounts, concentrations, or ratios stipulated herein in relation to the polar ionisable amino acid alone.

Suitably, the liquid pharmaceutical composition comprises a polar ionisable amino acid (optionally in combination with a non-polar amino acid as defined above) at a concentration of from about 1 to 50 mM, more suitably from about 10 to 40 mM, most suitably from about 20 mM to 30 mM. In a particular embodiment, the liquid pharmaceutical composition comprises a polar ionisable amino acid (optionally in combination with a non-polar amino acid as defined above) at a concentration of about 25 mM.

Suitably, the liquid pharmaceutical composition comprises the polar ionisable amino acid (optionally in combination with a non-polar amino acid as defined above) in a molar ratio of polar ionisable amino acid (optionally in combination with a non-polar amino acid as defined above) to etanercept of from about 5:1 to about 100:1. In an embodiment, the polar ionisable amino acid (optionally in combination with a non-polar amino acid as defined above) is present in a molar ratio of polar ionisable amino acid (optionally in combination with a non-polar amino acid as defined above) to etanercept of from about 10:1 to about 50:1, most suitably about 25:1.

The amino acid(s) described in this section may be suitably provided in zwitterionic form or a salt form (e.g. HCl salt). Suitably, unless stated otherwise, any amounts or concentrations (whether absolute or relative) given herein in relation to amino acids suitably refer to the amounts or concentrations of the respective free zwitterionic amino acids, even though said amino acids may be provided in a different form or may even exist within the liquid pharmaceutical composition in a different form at the prevailing pH.

Diluent

The liquid pharmaceutical compositions of the invention may include one or more pharmaceutically acceptable diluents. However, most suitably the liquid pharmaceutical composition is an aqueous pharmaceutical composition. Most suitably the diluent is water, and suitably water alone. The water is suitably water for injection (WFI).

Suitably the diluent may constitute the balance of ingredients in any liquid pharmaceutical composition, for instance so that the weight percentages total 100%. Suitably any concentrations given herein in relation to any component of the liquid pharmaceutical composition represent concentrations of said component in (and suitably dissolved in) the diluent in admixture with any other components.

The liquid pharmaceutical composition of the invention is suitably a solution, and is suitably (substantially or entirely) free of particulates or precipitates.

Absent or Low Level Components

Low/No Arginine Content

Suitably the liquid pharmaceutical composition is either (substantially or entirely) free of arginine or comprises arginine in a concentration of at most 0.1 mM, more suitably at most 0.01 mM, most suitably at most 0.001 mM.

Suitably the liquid pharmaceutical composition is either (substantially or entirely) free of arginine or comprises arginine in a molar ratio of arginine to buffer system of at most 1:150 (i.e. less than or equal to one mole of arginine for every 150 moles of buffer system), more suitably at most 1:1500, most suitably at most 1:15,000.

Suitably the liquid pharmaceutical composition is either (substantially or entirely) free of arginine or comprises arginine in a weight ratio of arginine to etanercept of at most 1:3000 (i.e. less than or equal to one part by weight of arginine for every 3000 parts by weight etanercept), more suitably at most 1:30,000, most suitably at most 1:300,000.

Suitably the liquid pharmaceutical composition is either (substantially or entirely) free of arginine or comprises arginine in a molar ratio of arginine to etanercept of at most 1:3.75 (i.e. less than or equal to one mole of amino acid(s) for every 3.75 moles etanercept), more suitably at most 1:37.5, most suitably at most 1:375.

As explained herein, such references to "amino acids" (in this case arginine) in the context of their presence or otherwise within liquid pharmaceutical compositions relate to the corresponding free amino acid(s) and not amino acid residue(s) covalently incorporated as part of a larger compound, such as a peptide or protein.

As illustrated in the Example section, liquid pharmaceutical compositions of the invention which (substantially or entirely) exclude arginine perform particularly well in stress tests, and are much more stable with respect to aggregation, fragmentation and protein unfolding than expected in view of the prior art.

Low/No Sulphur-Containing Amino Acid Content

Suitably the liquid pharmaceutical composition is either (substantially or entirely) free of sulphur-containing amino acid(s) (e.g. cysteine or methionine, especially methionine) or comprises sulphur-containing amino acid(s) (e.g. cysteine or methionine, especially methionine) in a concentration of at most 0.1 mM, more suitably at most 0.01 mM, most suitably at most 0.001 mM.

Suitably the liquid pharmaceutical composition is either (substantially or entirely) free of sulphur-containing amino acid(s) (e.g. cysteine or methionine, especially methionine) or comprises sulphur-containing amino acid(s) (e.g. cysteine or methionine, especially methionine) in a molar ratio of sulphur-containing amino acid(s) to buffer system of at most 1:150 (i.e. less than or equal to one mole of sulphur-containing amino acid(s) for every 150 moles of buffer system), more suitably at most 1:1500, most suitably at most 1:15,000.

Suitably the liquid pharmaceutical composition is either (substantially or entirely) free of sulphur-containing amino acid(s) (e.g. cysteine or methionine, especially methionine) or comprises sulphur-containing amino acid(s) (e.g. cysteine or methionine, especially methionine) in a weight ratio of sulphur-containing amino acid(s) to etanercept of at most 1:3000 (i.e. less than or equal to one part by weight of sulphur-containing amino acid(s) for every 3000 parts by weight etanercept), more suitably at most 1:30,000, most suitably at most 1:300,000.

Suitably the liquid pharmaceutical composition is either (substantially or entirely) free of sulphur-containing amino acid(s) or comprises sulphur-containing amino acid(s) in a molar ratio of sulphur-containing amino acid(s) to etanercept of at most 1:3.75 (i.e. less than or equal to one mole of amino acid(s) for every 3.75 moles etanercept), more suitably at most 1:37.5, most suitably at most 1:375.

Suitably the liquid pharmaceutical composition is either (substantially or entirely) free of cysteine and/or methionine (most preferably both), or comprises cysteine and/or methionine (most preferably both) in an amount, concentration, molar ratio, or weight ratio of at most that stipulated in any of the preceding paragraphs of this sub-section in relation to "sulphur-containing amino acid(s)" more generally.

As explained herein, such references to "amino acids" (in this case sulphur-containing amino acid(s)) in the context of their presence or otherwise within liquid pharmaceutical compositions relate to the corresponding free amino acid(s) and not amino acid residue(s) covalently incorporated as part of a larger compound, such as a peptide or protein.

As illustrated in the Example section, liquid pharmaceutical compositions of the invention which (substantially or entirely) exclude sulphur-containing amino acid(s) (e.g. cysteine or methionine, especially methionine) perform particularly well in stress tests.

Low/No Non-Stipulated Amino Acids

Suitably the liquid pharmaceutical composition is either (substantially or entirely) free of non-stipulated amino acid(s) (i.e. amino acids other than those stipulated as being present) or comprises non-stipulated amino acid(s) in a concentration of at most 0.1 mM, more suitably at most 0.01 mM, most suitably at most 0.001 mM.

As explained herein, such references to "amino acids" (in this case non-stipulated amino acid(s)) in the context of their presence or otherwise within liquid pharmaceutical compositions relate to the corresponding free amino acid(s) and not amino acid residue(s) covalently incorporated as part of a larger compound, such as a peptide or protein.

Low/No Surfactants

Suitably the liquid pharmaceutical composition is either (substantially or entirely) free of surfactants (whether cationic, anionic, amphoteric, or non-ionic) or comprises one or more of said surfactants in a (collective) concentration of at most 1 mM, more suitably at most 0.1 mM, more suitably at most 0.01 mM, more suitably at most 0.001 mM, most suitably at most 0.0001 mM.

Suitably the liquid pharmaceutical composition is either (substantially or entirely) free of surfactants (whether cationic, anionic, amphoteric, or non-ionic) or comprises one or more of said surfactants in a (collective) molar ratio of surfactant(s) to buffer system of at most 1:10, more suitably at most 1:100, most suitably at most 1:1000, more suitably at most 1:10,000, suitably at most 1:100,000.

Suitably the liquid pharmaceutical composition is either (substantially or entirely) free of surfactants (whether cationic, anionic, amphoteric, or non-ionic) or comprises one or more of said surfactants in a (collective) weight ratio of surfactant(s) to etanercept of at most 1:50 (i.e. less than or equal to one part by weight of surfactant(s) for every 50 parts by weight etanercept), more suitably at most 1:500, more suitably at most 1:5000, more suitably at most 1:50,000, suitably at most 1:500,000.

Suitably the liquid pharmaceutical composition is either (substantially or entirely) free of surfactants (whether cationic, anionic, amphoteric, or non-ionic) or comprises one or more of said surfactants in a (collective) molar ratio of surfactant(s) to etanercept of at most 3:1, more suitably at most 0.3:1, more suitably 0.003:1, more suitably 0.0003:1, suitably 0.00003:1.

Suitably, the surfactant(s) referred to in this section (and thereby deemed absent or present in only very low quantities) may be cationic, anionic, amphoteric, or non-ionic surfactants. Suitably, the surfactant(s) referred to in this section (and deemed absent or present in only very low quantities) are non-ionic surfactants (e.g. polysorbates or spans). Therefore, the liquid pharmaceutical composition is suitably (substantially or entirely) free of non-ionic surfactants (especially polysorbate 20 and polysorbate 80), or or comprises one or more of said non-ionic surfactants in an amount, concentration, molar ratio, or weight ratio of at most that stipulated in any of the preceding paragraphs of this sub-section in relation to "surfactant(s)" more generally.

As illustrated in the Example section, liquid pharmaceutical compositions of the invention which (substantially or entirely) exclude surfactants or certain surfactants, as defined above, perform particularly well in stress tests. This may be considered surprising in view of the prior art, which often employs a surfactant where arginine is absent.

Low/No Nitrogen-Containing Chelating Agents

Suitably the liquid pharmaceutical composition is either (substantially or entirely) free of nitrogen-containing chelating agent(s) (e.g. EDTA or salts thereof) or comprises nitrogen-containing chelating agent(s) (e.g. EDTA or salts thereof) in a concentration of at most 0.1 mM, more suitably at most 0.01 mM, most suitably at most 0.001 mM.

Suitably the liquid pharmaceutical composition is either (substantially or entirely) free of nitrogen-containing chelating agent(s) (e.g. EDTA or salts thereof) or comprises nitrogen-containing chelating agent(s) (e.g. EDTA or salts thereof) in a molar ratio of nitrogen-containing chelating agent(s) (e.g. EDTA or salts thereof) to buffer system of at most 1:150 (i.e. less than or equal to one mole of nitrogen-containing chelating agent(s) for every 150 moles of buffer system), more suitably at most 1:1500, most suitably at most 1:15,000.

Suitably the liquid pharmaceutical composition is either (substantially or entirely) free of nitrogen-containing chelating agent(s) (e.g. EDTA or salts thereof) or comprises nitrogen-containing chelating agent(s) (e.g. EDTA or salts thereof) in a weight ratio of nitrogen-containing chelating agent(s) (e.g. EDTA or salts thereof) to etanercept of at most 1:3000 (i.e. less than or equal to one part by weight of nitrogen-containing chelating agent(s) for every 3000 parts by weight etanercept), more suitably at most 1:30,000, most suitably at most 1:300,000.

Suitably the liquid pharmaceutical composition is either (substantially or entirely) free of nitrogen-containing chelating agent(s) (e.g. EDTA or salts thereof) or comprises nitrogen-containing chelating agent(s) (e.g. EDTA or salts thereof) in a molar ratio of nitrogen-containing chelating agent(s) (e.g. EDTA or salts thereof) to etanercept of at most 1:3.75 (i.e. less than or equal to one mole of nitrogen-containing chelating agent(s) for every 3.75 moles of etanercept), more suitably at most 1:37.5, most suitably at most 1:375.

Suitably the liquid pharmaceutical composition is either (substantially or entirely) free of EDTA or a salt thereof, or comprises EDTA or a salt thereof in an amount, concentration, molar ratio, or weight ratio of at most that stipulated in any of the preceding paragraphs of this sub-section in relation to "nitrogen-containing chelating agent(s)" more generally.

Such references to "nitrogen-containing chelating agent(s)" in the context of their presence or otherwise within liquid pharmaceutical compositions relate to the corresponding free chelating agent(s) and not chelating residues covalently incorporated as part of a peptide or protein.

As illustrated in the Example section, liquid pharmaceutical compositions of the invention which (substantially or entirely) exclude nitrogen-containing chelating agent(s) (e.g. EDTA) perform particularly well in stress tests.

Particular Embodiments

In a particular embodiment, the liquid pharmaceutical composition comprises a citrate buffer system and one of either hisidine or aspartic acid as a polar ionisable amino acid. In a particular embodiment, the liquid pharmaceutical composition comprises a citrate buffer system and hisidine as a polar ionisable amino acid.

In a particular embodiment, the liquid pharmaceutical composition comprises a phosphate buffer system and either: is (substantially or entirely) free of any amino acids; comprises aspartic acid (and suitably no other amino acids); or comprises a combination of lysine and proline (and suitably no other amino acids).

The molar concentrations of the stabiliser (e.g. sucrose) and tonicifier (e.g. sodium chloride) may be interrelated by Equation (1):

$$[\text{stabiliser}]_{mol} * [\text{tonicifier}]_{mol} = A_{mol} * 2^n \qquad \text{Equation (1)}$$

where $[\text{stabiliser}]_{mol}$ is the molar concentration of the stabiliser; $[\text{tonicifier}]_{mol}$ is the molar concentration of the tonicifier; $A_{mol}$ is a baseline molar concentration constant (the product of molar concentrations when n=0); and n is any number (positive or negative).

The weight concentrations of the stabiliser (e.g. sucrose) and tonicifier (e.g. sodium chloride) may be interrelated by Equation (2):

$$[\text{stabiliser}]_{wt}[\text{tonicifier}]_{wt} = A_{wt} * 2^n \qquad \text{Equation (2)}$$

where $[\text{stabiliser}]_{wt}$ is the weight concentration of the stabiliser; $[\text{tonicifier}]_{wt}$ is the weight concentration of the tonicifier; $A_{wt}$ is a baseline weight concentration constant (the product of weight concentrations when n=0); and n is any number (positive or negative).

In relation to Equation (1), suitably $A_{mol}$ is between 1000 and 5000 mM² (units=square millimoles, mM²) suitably between 2000 and 4000 mM², more suitably between 2900 and 3100 mM², most suitably about 3000 mM².

In relation to equation (1), suitably n is a number between −5 and +5, suitably a number between −2 and +2, more suitably a number between −1 and +1, most suitably either 0 or 1.

In relation to Equation (2), suitably $A_{wt}$ is between 20 and 100 (mg/mL)² (units=square milligrams per milliliter, (mg/mL)²) suitably between 40 and 80 (mg/mL)², more suitably between 50 and 70 (mg/mL)², most suitably about 58 (mg/mL)².

In relation to equation (2), suitably n is a number between −5 and +5, suitably a number between −2 and +2, more suitably a number between −1 and +1, most suitably either 0 or 1.

By way of Example, molar weights and concentrations of sucrose (stabiliser) and sodium chloride (tonicifier) may be interrelated as follows:

| n | Sucrose (mM) | NaCl (mM) | Sucrose (mg/mL) | NaCl (mg/mL) |
|---|---|---|---|---|
| −1 | 7.5 | 200 | 2.5 | 11.68 |
| 0 | 30 | 100 | 10 | 5.84 |
| 1 | 120 | 50 | 40 | 2.92 |
| 2 | 480 | 25 | 160 | 1.46 | where $A_{mol}$ is 3000 mM² and $A_{wt}$ is 58 (mg/mL)².

Varying the molar or weight concentrations of the sugar and salt in accordance with Equations (1) and/or (2) generally produces liquid pharmaceutical compositions exhibiting viable performance and storage characteristics.

In preferred embodiments, the minimum weight concentration of stabiliser is 0.5 wt %. In preferred embodiments, the minimum molar concentration of stabiliser is 15 mM. In preferred embodiments, the minimum weight concentration of stabiliser is 5 mg/mL.

In an embodiment, the liquid pharmaceutical composition comprises:
  etanercept;
  a buffer system (e.g. phosphate buffer or citrate buffer);
  a tonicifier (e.g. sodium chloride);
  a sugar stabiliser (e.g. sucrose and/or trehalose); and
  water (for injection);
wherein the composition has a pH between pH 6.1 and 6.5; and
wherein the composition is either (substantially or entirely) free of amino acid(s) or comprises (preferably as substantially or entirely the only amino acid(s)) a polar ionisable natural amino acid and optionally an additional non-polar amino acid.

In an embodiment, the liquid pharmaceutical composition comprises:
  etanercept;
  a buffer system (e.g. phosphate buffer or a citrate buffer);
  a tonicifier (e.g. sodium chloride);
  a sugar stabiliser (e.g. sucrose and/or trehalose); and
  water (for injection);
wherein the composition has a pH between pH 6.1 and 6.5; and
wherein the composition is either (substantially or entirely) free of amino acid(s) or comprises (preferably as substantially or entirely the only amino acid(s)) a polar ionisable natural amino acid and optionally an additional non-polar amino acid;
wherein the composition is either (substantially or entirely) free of arginine or comprises arginine in a concentration of at most 0.1 mM, more suitably at most 0.01 mM, most suitably at most 0.001 mM;
wherein the composition is either (substantially or entirely) free of sulphur-containing amino acid(s) (especially methionine) or comprises sulphur-containing amino acid(s) in a concentration of at most 0.1 mM, more suitably at most 0.01 mM, most suitably at most 0.001 mM;
wherein the composition is either (substantially or entirely) free of surfactants (especially non-ionic surfactants such as polysorbates and spans) or comprises one or more of said surfactants in a (collective) concentration of at most 1 mM, more suitably at most 0.1 mM, more suitably at most 0.01 mM, more suitably at most 0.001 mM, most suitably at most 0.0001 mM; and
wherein the composition is either (substantially or entirely) free of nitrogen-containing chelating agent(s) (especially EDTA or salts thereof) or comprises nitrogen-containing chelating agent(s) in a concentration of at most 0.1 mM, more suitably at most 0.01 mM, most suitably at most 0.001 mM.

In an embodiment, the liquid pharmaceutical composition comprises:
  etanercept;
  a buffer system (e.g. phosphate buffer or citrate buffer);
  a tonicifier (e.g. sodium chloride);
  a sugar stabiliser (e.g. sucrose and/or trehalose); and
  water (for injection);
wherein the composition has a pH between pH 6.1 and 6.5; and
wherein the molar concentrations of the stabiliser (e.g. sucrose) and tonicifier (e.g. sodium chloride) are interrelated by Equation (1):

$$[\text{stabiliser}]_{mol} * [\text{tonicifier}]_{mol} = A_{mol} * 2^n \quad \text{Equation (1)}$$

where $[\text{stabiliser}]_{mol}$ is the molar concentration of the stabiliser; $[\text{tonicifier}]_{mol}$ is the molar concentration of the tonicifier; $A_{mol}$ is a baseline molar concentration constant between 2000 and 4000 mM$^2$; and n is a number between −2 and +2;
wherein the composition is either (substantially or entirely) free of amino acid(s) or comprises (preferably as substantially or entirely the only amino acid(s)) a polar ionisable natural amino acid in a concentration of between 10 and 30 mM and optionally an additional non-polar amino acid in a concentration of between 10 and 30 mM;

In an embodiment, the liquid pharmaceutical composition comprises:
  etanercept;
  a buffer system (e.g. phosphate buffer or a citrate buffer);
  a tonicifier (e.g. sodium chloride);
  a sugar stabiliser (e.g. sucrose and/or trehalose); and
  water (for injection);
wherein the composition has a pH between pH 6.1 and 6.5;
wherein the molar concentrations of the stabiliser (e.g. sucrose) and tonicifier (e.g. sodium chloride) are interrelated by Equation (1):

$$[\text{stabiliser}]_{mol} * [\text{tonicifier}]_{mol} = A_{mol} * 2^n \quad \text{Equation (1)}$$

where $[\text{stabiliser}]_{mol}$ is the molar concentration of the stabiliser; $[\text{tonicifier}]_{mol}$ is the molar concentration of the tonicifier; $A_{mol}$ is a baseline molar concentration constant between 2000 and 4000 mM$^2$; and n is a number between −2 and +2;
wherein the composition is either (substantially or entirely) free of amino acid(s) or comprises (preferably as substantially or entirely the only amino acid(s)) a polar ionisable natural amino acid in a concentration of between 10 and 30 mM and optionally an additional non-polar amino acid in a concentration of between 10 and 30 mM;
wherein the composition is either (substantially or entirely) free of arginine or comprises arginine in a concentration of at most 0.1 mM, more suitably at most 0.01 mM, most suitably at most 0.001 mM;
wherein the composition is either (substantially or entirely) free of sulphur-containing amino acid(s) (especially methionine) or comprises sulphur-containing amino acid(s) in a concentration of at most 0.1 mM, more suitably at most 0.01 mM, most suitably at most 0.001 mM;
wherein the composition is either (substantially or entirely) free of surfactants (especially non-ionic surfactants such as polysorbates and spans) or comprises one or more of said surfactants in a (collective) concentration of at most 1 mM, more suitably at most 0.1 mM, more suitably at most 0.01 mM, more suitably at most 0.001 mM, most suitably at most 0.0001 mM; and
wherein the composition is either (substantially or entirely) free of nitrogen-containing chelating agent(s) (especially EDTA or salts thereof) or comprises nitrogen-containing chelating agent(s) in a concentration of at most 0.1 mM, more suitably at most 0.01 mM, most suitably at most 0.001 mM.

In an embodiment, the liquid pharmaceutical composition comprises:
  etanercept;
  a buffer system (e.g. phosphate buffer or citrate buffer);
  a tonicifier (e.g. sodium chloride);
  a sugar stabiliser (e.g. sucrose and/or trehalose); and
  water (for injection);
wherein the composition has a pH between pH 6.1 and 6.5; and
wherein the composition is either (substantially or entirely) free of amino acid(s) or comprises (preferably as substantially or entirely the only amino acid(s)) either:

asparatic acid (preferably with a phosphate buffer);
histidine (preferably with a citrate buffer); or
a combination of lysine and proline.

In an embodiment, the liquid pharmaceutical composition comprises:
  etanercept;
  a buffer system (e.g. phosphate buffer or a citrate buffer);
  a tonicifier (e.g. sodium chloride);
  a sugar stabiliser (e.g. sucrose and/or trehalose); and
  water (for injection);
wherein the composition has a pH between pH 6.1 and 6.5; and
wherein the composition is either (substantially or entirely) free of amino acid(s) or comprises (preferably as substantially or entirely the only amino acid(s)) either:
  asparatic acid (preferably with a phosphate buffer);
  histidine (preferably with a citrate buffer); or
  a combination of lysine and proline; and
wherein the composition is either (substantially or entirely) free of arginine or comprises arginine in a concentration of at most 0.1 mM, more suitably at most 0.01 mM, most suitably at most 0.001 mM;
wherein the composition is either (substantially or entirely) free of sulphur-containing amino acid(s) (especially methionine) or comprises sulphur-containing amino acid(s) in a concentration of at most 0.1 mM, more suitably at most 0.01 mM, most suitably at most 0.001 mM;
wherein the composition is either (substantially or entirely) free of surfactants (especially non-ionic surfactants such as polysorbates and spans) or comprises one or more of said surfactants in a (collective) concentration of at most 1 mM, more suitably at most 0.1 mM, more suitably at most 0.01 mM, more suitably at most 0.001 mM, most suitably at most 0.0001 mM; and
wherein the composition is either (substantially or entirely) free of nitrogen-containing chelating agent(s) (especially EDTA or salts thereof) or comprises nitrogen-containing chelating agent(s) in a concentration of at most 0.1 mM, more suitably at most 0.01 mM, most suitably at most 0.001 mM.

In an embodiment, the liquid pharmaceutical composition comprises:
  40-60 mg/mL (or alternatively 20-30 mg/mL) etanercept;
  20-30 mM buffer system (e.g. phosphate buffer or citrate buffer);
  40-120 mM tonicifier (e.g. sodium chloride) (suitably 40-60 mM or 90-110 mM);
  0.5-5.0 wt % sugar stabiliser (e.g. sucrose and/or trehalose) (suitably 0.5 to 1.5 wt % or 3.5 to 4.5 wt %); and
  water (for injection);
wherein the composition has a pH between pH 6.1 and 6.5; and
wherein the composition is either (substantially or entirely) free of amino acid(s) or comprises (preferably as substantially or entirely the only amino acid(s)) either:
  20-30 mM asparatic acid (preferably with a phosphate buffer);
  20-30 mM histidine (preferably with a citrate buffer); or
  a combination of 10-15 mM lysine and 10-15 mM proline.

In an embodiment, the liquid pharmaceutical composition comprises:
  40-60 mg/mL (or alternatively 20-30 mg/mL) etanercept;
  20-30 mM buffer system (e.g. phosphate buffer or a citrate buffer);
  40-120 mM tonicifier (e.g. sodium chloride) (suitably 40-60 mM or 90-110 mM);
  0.5-5.0 wt % sugar stabiliser (e.g. sucrose and/or trehalose) (suitably 0.5 to 1.5 wt % or 3.5 to 4.5 wt %); and
  water (for injection);
wherein the composition has a pH between pH 6.1 and 6.5; and
wherein the composition is either (substantially or entirely) free of amino acid(s) or comprises (preferably as substantially or entirely the only amino acid(s)) either:
  20-30 mM asparatic acid (preferably with a phosphate buffer);
  20-30 mM histidine (preferably with a citrate buffer); or
  a combination of 10-15 mM lysine and 10-15 mM proline; and
wherein the composition is either (substantially or entirely) free of arginine or comprises arginine in a concentration of at most 0.1 mM, more suitably at most 0.01 mM, most suitably at most 0.001 mM;
wherein the composition is either (substantially or entirely) free of sulphur-containing amino acid(s) (especially methionine) or comprises sulphur-containing amino acid(s) in a concentration of at most 0.1 mM, more suitably at most 0.01 mM, most suitably at most 0.001 mM;
wherein the composition is either (substantially or entirely) free of surfactants (especially non-ionic surfactants such as polysorbates and spans) or comprises one or more of said surfactants in a (collective) concentration of at most 1 mM, more suitably at most 0.1 mM, more suitably at most 0.01 mM, more suitably at most 0.001 mM, most suitably at most 0.0001 mM; and
wherein the composition is either (substantially or entirely) free of nitrogen-containing chelating agent(s) (especially EDTA or salts thereof) or comprises nitrogen-containing chelating agent(s) in a concentration of at most 0.1 mM, more suitably at most 0.01 mM, most suitably at most 0.001 mM.

In an embodiment, the liquid pharmaceutical composition consists essentially of:
  40-60 mg/mL (or alternatively 20-30 mg/mL) etanercept;
  20-30 mM buffer system (e.g. phosphate buffer or a citrate buffer);
  40-120 mM tonicifier (sodium chloride);
  0.5-5.0 wt % sugar stabiliser (e.g. sucrose and/or trehalose); and
  water (for injection);
wherein the composition has a pH between pH 6.1 and 6.5; and
wherein the composition is either (substantially or entirely) free of amino acid(s) or comprises (preferably as substantially or entirely the only amino acid(s)) either:
  20-30 mM asparatic acid (preferably with a phosphate buffer);
  20-30 mM histidine (preferably with a citrate buffer); or
  a combination of 10-15 mM lysine and 10-15 mM proline.

In an embodiment, the liquid pharmaceutical composition consists essentially of:
  45-55 mg/mL (or alternatively 20-30 mg/mL) etanercept;
  20-30 mM buffer system (e.g. phosphate buffer);
  90-110 mM tonicifier (e.g. sodium chloride);
  0.9-1.1 wt % (or 30 mM+/−5 mM) sugar stabiliser (e.g. sucrose and/or trehalose); and
  water (for injection);
wherein the composition has a pH between pH 6.1 and 6.5.

In an embodiment, the liquid pharmaceutical composition consists essentially of:
  45-55 mg/mL (or alternatively 20-30 mg/mL) etanercept;
  20-30 mM buffer system (e.g. phosphate buffer)

90-110 mM tonicifier (e.g. sodium chloride);
0.9-1.1 wt % (or 30 mM+/−5 mM) sugar stabiliser (e.g. sucrose and/or trehalose);
20-30 mM asparatic acid; and
water (for injection);
wherein the composition has a pH of between pH 6.1 and 6.5.

In an embodiment, the liquid pharmaceutical composition consists essentially of:
45-55 mg/mL (or alternatively 20-30 mg/mL) etanercept;
20-30 mM buffer system (e.g. citrate buffer);
90-110 mM tonicifier (e.g. sodium chloride);
0.9-1.1 wt % (or 30 mM+/−5 mM) sugar stabiliser (e.g. sucrose and/or trehalose);
20-30 mM histidine; and
water (for injection);
wherein the composition has a pH of between pH 6.1 and 6.5.

In an embodiment, the liquid pharmaceutical composition consists essentially of:
45-55 mg/mL (or alternatively 20-30 mg/mL) etanercept;
20-30 mM buffer system (e.g. phosphate buffer);
45-55 mM tonicifier (e.g. sodium chloride);
3.5-4.5 wt % (or 120 mM+/−30 mM) sugar stabiliser (e.g. sucrose and/or trehalose);
10-15 mM lysine;
10-15 mM proline; and
water (for injection);
wherein the composition has a pH of between pH 6.1 and 6.5.

In an embodiment, the liquid pharmaceutical composition consists essentially of:
50 mg/mL (or alternatively 25 mg/mL) etanercept;
25 mM buffer system (e.g. phosphate buffer)
100 mM tonicifier (e.g. sodium chloride);
1 wt % (or 30 mM+/−1 mM) sugar stabiliser (e.g. sucrose and/or trehalose); and
water (for injection);
wherein the composition has a pH of 6.3.

In an embodiment, the liquid pharmaceutical composition consists essentially of:
50 mg/mL (or alternatively 25 mg/mL) etanercept;
25 mM buffer system (e.g. phosphate buffer);
100 mM tonicifier (e.g. sodium chloride);
1 wt % (or 30 mM+/−1 mM) sugar stabiliser (e.g. sucrose and/or trehalose);
25 mM asparatic acid; and
water (for injection);
wherein the composition has a pH of 6.3.

In an embodiment, the liquid pharmaceutical composition consists essentially of:
50 mg/mL (or alternatively 25 mg/mL) etanercept;
25 mM buffer system (e.g. citrate buffer);
100 mM tonicifier (e.g. sodium chloride);
1 wt % (or 30 mM+/−1 mM) sugar stabiliser (e.g. sucrose and/or trehalose);
25 mM histidine; and
water (for injection);
wherein the composition has a pH of 6.3.

In an embodiment, the liquid pharmaceutical composition consists essentially of:
50 mg/mL (or alternatively 25 mg/mL) etanercept;
25 mM buffer system (e.g. phosphate buffer)
50 mM tonicifier (e.g. sodium chloride);
4 wt % (or 120 mM+/−4 mM) sugar stabiliser (e.g. sucrose and/or trehalose);
12.5 mM lysine;
12.5 mM proline; and
water (for injection);
wherein the composition has a pH of 6.3.

In an embodiment, the liquid pharmaceutical composition comprises:
40-60 mg/mL (or alternatively 20-30 mg/mL) etanercept;
20-30 mM buffer system selected from a phosphate buffer system or a citrate buffer system;
40-120 mM sodium chloride (suitably 40-60 mM or 90-110 mM);
0.5-5.0 wt % sucrose (suitably 0.5 to 1.5 wt % or 3.5 to 4.5 wt %); and
water (for injection);
wherein the composition has a pH between pH 6.1 and 6.5; and
wherein the composition is either (substantially or entirely) free of amino acid(s) or comprises (preferably as substantially or entirely the only amino acid(s)) either:
20-30 mM asparatic acid (preferably with a phosphate buffer);
20-30 mM histidine (preferably with a citrate buffer); or
a combination of 10-15 mM lysine and 10-15 mM proline.

In an embodiment, the liquid pharmaceutical composition comprises:
40-60 mg/mL (or alternatively 20-30 mg/mL) etanercept;
20-30 mM buffer system selected from a phosphate buffer system or a citrate buffer system;
40-120 mM sodium chloride (suitably 40-60 mM or 90-110 mM);
0.5-5.0 wt % sucrose (suitably 0.5 to 1.5 wt % or 3.5 to 4.5 wt %); and
water (for injection);
wherein the composition has a pH between pH 6.1 and 6.5; and
wherein the composition is either (substantially or entirely) free of amino acid(s) or comprises (preferably as substantially or entirely the only amino acid(s)) either:
20-30 mM asparatic acid (preferably with a phosphate buffer);
20-30 mM histidine (preferably with a citrate buffer); or
a combination of 10-15 mM lysine and 10-15 mM proline; and
wherein the composition is either (substantially or entirely) free of arginine or comprises arginine in a concentration of at most 0.1 mM, more suitably at most 0.01 mM, most suitably at most 0.001 mM;
wherein the composition is either (substantially or entirely) free of sulphur-containing amino acid(s) (especially methionine) or comprises sulphur-containing amino acid(s) in a concentration of at most 0.1 mM, more suitably at most 0.01 mM, most suitably at most 0.001 mM;
wherein the composition is either (substantially or entirely) free of surfactants (especially non-ionic surfactants such as polysorbates and spans) or comprises one or more of said surfactants in a (collective) concentration of at most 1 mM, more suitably at most 0.1 mM, more suitably at most 0.01 mM, more suitably at most 0.001 mM, most suitably at most 0.0001 mM; and
wherein the composition is either (substantially or entirely) free of nitrogen-containing chelating agent(s) (especially EDTA or salts thereof) or comprises nitrogen-containing chelating agent(s) in a concentration of at most 0.1 mM, more suitably at most 0.01 mM, most suitably at most 0.001 mM.

In an embodiment, the liquid pharmaceutical composition consists essentially of:
- 40-60 mg/mL (or alternatively 20-30 mg/mL) etanercept;
- 20-30 mM buffer system selected from a phosphate buffer system or a citrate buffer system;
- 40-120 mM sodium chloride;
- 0.5-5.0 wt % sucrose; and
- water (for injection);

wherein the composition has a pH between pH 6.1 and 6.5; and
wherein the composition is either (substantially or entirely) free of amino acid(s) or comprises (preferably as substantially or entirely the only amino acid(s)) either:
- 20-30 mM asparatic acid (preferably with a phosphate buffer);
- 20-30 mM histidine (preferably with a citrate buffer); or
- a combination of 10-15 mM lysine and 10-15 mM proline.

In an embodiment, the liquid pharmaceutical composition consists essentially of:
- 45-55 mg/mL (or alternatively 20-30 mg/mL) etanercept;
- 20-30 mM phosphate buffer system (suitably sodium phosphate(s) as buffering agent);
- 90-110 mM sodium chloride;
- 0.9-1.1 wt % (or 30 mM+/−5 mM) sucrose; and
- water (for injection);

wherein the composition has a pH between pH 6.1 and 6.5.

In an embodiment, the liquid pharmaceutical composition consists essentially of:
- 45-55 mg/mL (or alternatively 20-30 mg/mL) etanercept;
- 20-30 mM phosphate buffer system (suitably sodium phosphate(s) as buffering agent);
- 90-110 mM sodium chloride;
- 0.9-1.1 wt % (or 30 mM+/−5 mM) sucrose;
- 20-30 mM asparatic acid; and
- water (for injection);
    wherein the composition has a pH of between pH 6.1 and 6.5.

In an embodiment, the liquid pharmaceutical composition consists essentially of:
- 45-55 mg/mL (or alternatively 20-30 mg/mL) etanercept;
- 20-30 mM citrate buffer system (suitably sodium citrate(s) as buffering agent);
- 90-110 mM sodium chloride;
- 0.9-1.1 wt % (or 30 mM+/−5 mM) sucrose;
- 20-30 mM histidine; and
- water (for injection);

wherein the composition has a pH of between pH 6.1 and 6.5.

In an embodiment, the liquid pharmaceutical composition consists essentially of:
- 45-55 mg/mL (or alternatively 20-30 mg/mL) etanercept;
- 20-30 mM phosphate buffer system (suitably sodium phosphate(s) as buffering agent);
- 45-55 mM sodium chloride;
- 3.5-4.5 wt % (or 120 mM+/−30 mM) sucrose;
- 10-15 mM lysine;
- 10-15 mM proline; and
- water (for injection);

wherein the composition has a pH of between pH 6.1 and 6.5.

In an embodiment, the liquid pharmaceutical composition consists essentially of:
- 50 mg/mL (or alternatively 25 mg/mL) etanercept;
- 25 mM phosphate buffer system (suitably sodium phosphate(s) as buffering agent);
- 100 mM sodium chloride;
- 1 wt % (or 30 mM+/−1 mM) sucrose; and
- water (for injection);

wherein the composition has a pH of 6.3.

In an embodiment, the liquid pharmaceutical composition consists essentially of:
- 50 mg/mL (or alternatively 25 mg/mL) etanercept;
- 25 mM phosphate buffer system (suitably sodium phosphate(s) as buffering agent);
- 100 mM sodium chloride;
- 1 wt % (or 30 mM+/−1 mM) sucrose;
- 25 mM asparatic acid; and
- water (for injection);
    wherein the composition has a pH of 6.3.

In an embodiment, the liquid pharmaceutical composition consists essentially of:
- 50 mg/mL (or alternatively 25 mg/mL) etanercept;
- 25 mM citrate buffer system (suitably sodium citrate(s) as buffering agent);
- 100 mM sodium chloride;
- 1 wt % (or 30 mM+/−1 mM) sucrose;
- 25 mM histidine; and
- water (for injection);

wherein the composition has a pH of 6.3.

In an embodiment, the liquid pharmaceutical composition consists essentially of:
- 50 mg/mL (or alternatively 25 mg/mL) etanercept;
- 25 mM phosphate buffer system (suitably sodium phosphate(s) as buffering agent);
- 50 mM sodium chloride;
- 4 wt % (or 120 mM+/−4 mM) sucrose;
- 12.5 mM lysine;
- 12.5 mM proline; and
- water (for injection);

wherein the composition has a pH of 6.3.

Suitably, the liquid pharmaceutical composition may be as set forth in any of the preceding embodiments except that, rather than being defined by the above-referenced amounts and/or concentrations of particular components (whether present or in minimal quantities), they are instead or additionally defined by reference to corresponding molar or weight ratios of the component to the buffer system; or corresponding molar or weight ratios of the component to etanercept. The skilled person will readily deduce for each component, from the relevant section of this specification relating to that specific component, which molar and weight ratios correspond to which concentrations.

It will be appreciated that the buffering agent or buffer system of any of the embodiments described herein may be directly incorporated into the compositions or may be produced in situ, for instance, via an acid base reaction, suitably by reacting either a conjugate acid (e.g. phosphoric or citric acid) with a base (e.g. sodium hydroxide); or a base/conjugate base (e.g. sodium phosphate species or sodium citrate species) with an acid (e.g. hydrochloric acid). Regardless of the method used to provide or produce the buffering agent or buffer system, suitably the resulting composition ultimately comprises an appropriate balance of the buffering agent and any acid/base conjugate to furnish the desired pH. The skilled person will be readily able to calculate or experimentally determine, without undue effort, the appropriate balance of buffering agent and acid/base conjugate, and/or the amount of base which needs to be added to a conjugate acid in order to produce the appropriate amount of buffering agent and furnish the desired pH.

Method of Manufacturing a Liquid Pharmaceutical Composition

The present invention provides a method of manufacturing a liquid pharmaceutical composition (suitably as defined herein) which suitably involves mixing together the respective ingredients stipulated in respect to the liquid pharmaceutical composition, optionally in any amount, concentration, or form stipulated; and optionally adjusting any one or more parameters given herein in relation to a liquid pharmaceutical composition (e.g. pH).

The method suitably comprises mixing together, in any particular order deemed appropriate, any relevant components required to form a liquid pharmaceutical composition as defined herein. The skilled person may refer to the Examples or techniques well known in the art for forming liquid pharmaceutical compositions (especially those for injection via syringe). Different embodiments will suitably require different combinations of components to be mixed, potentially in different amounts. The skilled person can readily deduce such combinations and amounts by reference to the foregoing disclosure relating to the liquid pharmaceutical composition.

Suitably the method involves mixing together the relevant components suitably, in a diluent (e.g. water), suitably so that all of the components are (substantially or entirely) dissolved in the diluent.

The method may involve first preparing a pre-mixture (or pre-solution) of some or all components (optionally with some or all of the diluent) excluding etanercept, and etanercept may then itself (optionally with or pre-dissolved in some of the diluent) be mixed with the pre-mixture (or pre-solution) to afford the liquid pharmaceutical composition, or a composition to which final components are then added to furnish the final liquid pharmaceutical composition. Most suitably, the pre-mixture contains all components except for the etanercept and optionally also some diluent (which may be used to pre-dissolve etanercept), suitably so that etanercept is added to a mixture which offers optimal stabilisation of etanercept. Suitably the aforementioned pre-mixture is prepared with the desired pH for the final liquid pharmaceutical formulation.

Suitably, the method involves forming a buffer system, suitably a buffer system comprising a buffering agent as defined herein. The buffer system is suitably formed in a pre-mixture prior to the addition of etanercept, though the buffer system may optionally be formed with etanercept present. The buffer system may be formed through simply mixing the buffering agent (supplied ready-made) with its acid/base conjugate (suitably in appropriate relative quantities to provide the desired pH—this can be determined by the skilled person either theoretically or experimentally). In the case of a phosphate (or citrate) buffer system, this may mean mixing together sodium phosphate (or sodium citrate) species and phosphoric acid (or citric acid). Alternatively, the buffer system may be formed through adding a strong acid (e.g. HCl) to the buffering agent (e.g. sodium phosphate species) in order to form in situ the acid/base conjugate (e.g. phosphoric acid or hydrogen phosphates) (again suitably in appropriate relative quantities to provide the desired pH). Alternatively, the buffer system may be formed through adding a strong base (e.g. sodium hydroxide) to the acid/base conjugate (e.g. phosphoric acid or hydrogen phosphate(s)) of the buffering agent (e.g. sodium phosphate(s)) in order to form in situ the buffering agent (again suitably in appropriate relative quantities to provide the desired pH). The pH of either the pre-mixture of final liquid pharmaceutical composition may be judiciously adjusted by adding the required quantity of strong base or strong acid, or even a quantity of buffering agent or acid/base conjugate.

In certain embodiments, the buffering agent and/or buffer system is pre-formed as a separate mixture, and the buffer system is transferred to a precursor of the liquid pharmaceutical composition (comprising some or all components save for the buffering agent and/or buffer system, suitably comprising etanercept and potentially only etanercept) via buffer exchange (e.g. using diafiltration until the relevant concentrations or osmolality is reached). Additional excipients may be added thereafter if necessary in order to produce the final liquid pharmaceutical composition. The pH may be adjusted once or before all the components are present.

Any, some, or all components may be pre-dissolved or pre-mixed with a diluent prior to mixing with other components.

The final liquid pharmaceutical composition may be filtered, suitably to remove particulate matter. Suitably filtration is through filters sized at or below 1 µm, suitably at 0.22 µm. Suitably, filtration is through either PES filters or PVDF filters, suitably with 0.22 µm PES filters.

The present invention also provides a liquid pharmaceutical composition obtainable by, obtained by, or directly obtained by the method of manufacture herein described.

Drug-Delivery Device

The present invention also provides a drug delivery device comprising a liquid pharmaceutical composition as defined herein. Suitably the drug delivery device comprises a chamber within which the pharmaceutical composition resides. Suitably the drug delivery device is sterile.

The drug delivery device may a vial, ampoule, syringe, injection pen (e.g. essentially incorporating a syringe), or intravenous bag. Most suitably the drug delivery device is a syringe, suitably an injection pen. Suitably the syringe is a glass syringe. Suitably the syringe comprises a needle, suitably a 29G ½" needle.

The present invention provides a method of manufacturing a drug delivery device, suitably as defined herein, the method comprising incorporating a liquid pharmaceutical composition as defined herein within a drug delivery device. Such manufacture typically involves charging the liquid pharmaceutical composition as defined herein to a syringe, suitably via a needle affixed thereto. The needle may thereafter be removed, replaced, or remain.

According to an eleventh aspect of the present invention there is provided a drug delivery device obtainable by, obtained by, or directly obtained by a method of manufacture defined herein.

Package

The present invention also provides a package comprising a liquid pharmaceutical composition as defined herein. Suitably the package comprises a drug delivery device as defined herein, suitably a plurality of drug delivery devices. The package may comprise any suitable container for containing one or more drug delivery devices.

The present invention provides a method of manufacturing a package, the method comprising incorporating a liquid pharmaceutical composition as defined herein within a package. Suitably this is achieved by incorporating said liquid pharmaceutical composition within one or more drug delivery devices, and thereafter incorporating the one or more pre-filled drug delivery devices into a container present within the package.

The package may suitably comprise instructions for using the liquid pharmaceutical composition, suitably for any one or more medical indications stipulated herein.

The present invention provides a package obtainable by, obtained by, or directly obtained by a method of manufacture defined herein.

Kit of Parts

The present invention also provides a kit of parts comprising a drug delivery device (without the liquid pharmaceutical composition incorporated therein), a liquid pharmaceutical composition as defined herein (optionally contained in a separate package or container), and optionally a set of instructions with directions regarding the administration (e.g. sub-cutaneous) of the liquid pharmaceutical composition. The user may then fill the drug delivery device with the liquid pharmaceutical composition (which may be provided in a vial or ampoule or such like) prior to administration.

Uses of Pharmaceutical Liquid Composition and Methods of Treatment

The present invention also provides:
- a method of treating a disease or medical disorder, suitably a tumour necrosis factor-alpha (TNF-α)-related autoimmune disease, suitably a disease selected from rheumatoid arthritis, juvenile rheumatoid arthritis, psoriatic arthritis, plaque psoriasis, and/or ankylosing spondylitis;
- a liquid pharmaceutical composition for use in therapy, suitably in the treatment of a tumour necrosis factor-alpha (TNF-α)-related autoimmune disease, suitably a disease selected from rheumatoid arthritis, juvenile rheumatoid arthritis, psoriatic arthritis, plaque psoriasis, and/or ankylosing spondylitis;
- a use of a liquid pharmaceutical compositions in the manufacture of a medicament for the treatment of a disease or disorder, suitably a tumour necrosis factor-alpha (TNF-α)-related autoimmune disease, suitably a disease selected from rheumatoid arthritis, juvenile rheumatoid arthritis, psoriatic arthritis, plaque psoriasis, and/or ankylosing spondylitis;

as defined anywhere herein.

The liquid pharmaceutical compositions are suitably parenterally administered, suitably via sub-cutaneous injection.

EXAMPLES

Materials and Equipment

The following samples were used in (or to produce) the Examples and Screening Experiments disclosed herein:

| Sample | Concentration/form |
| --- | --- |
| Enbrel ® 25 mg | 50 mg/mL liquid formulation 0.5 mL per syringe |

All excipients and ingredients used in the preparation of the Example formulations disclosed herein were readily commercially sourced.

The following equipment was used in the Examples and Screening Experiments disclosed herein:

| Method No. | Method | Purpose |
| --- | --- | --- |
| A1 | High performance size exclusion chromatography (HP-SEC) | Purity, monomer content, soluble aggregates |
| A2 | Hydrophobic interaction chromatography (HIC) | Changes in hydrophobicity, fragments/aggregates |
| A3 | Visual inspection (Ph.Eur.) | Visible particles |
| A4 | UV spectroscopy | Protein content in well plate, turbidity, aggregation index |
| A5 | SDS-PAGE | Covalent aggregation, fragmentation |

Analytical Techniques and Protocols

The individual protocols for each of the above analytical methods are described in turn below, and references in the Examples and Screening Experiments to any such analytical methods used these protocols.

Preparation of Analytical Samples

The analytical methods indicated above, and for which the protocols are provided below, were carried out on samples of each of the exemplified formulations, and described in more detail below, which were exposed to various stability test. Samples of each of these formulations were subjected to; $T_o$ (samples not subjected to any stress), $T_{mech}$ (samples subjected to mechanical stress), $T_{heat}$ (samples subjected to heat stress), $T_{1\ month}$ (samples stored at room temperature for 1 month).

After preparation, the formulations were filled into the syringes. In the mechanical stress test $T_{mech}$, the syringes were horizontally shaken for 2 hours in an IKA KS 4000ic control shaker at 25±3° C. and at 400 rpm. In the heat stress test $T_{heat}$, the syringes were placed for 1 week at 40° C. In the storage test $T_{1\ month}$, the syringes were stored for 1 month at 25° C. In the storage test $T_{3\ month}$, the syringes were stored for 3 months at 25° C.

A1—High Performance Size Exclusion Chromatography (HP-SEC)

HP-SEC was performed in accordance with the following protocols and parameters:
Instrument: HP1100 (Agilent Technologies)
Column: TSK gel Super SW3000 column (4.6 cm×300 mm)
Gel Filtration Standard: Bio-Rad product #151-1901, prepared by mixing 10 µl of gel filtration standard with 590 µl of 1×PBS (Dulbecco's PBS, Life Technologies, USA).
Injection volume: 10 µl.
Flow rate: 0.35 ml/min
Mobile phase: 50 mM sodium phosphate, 0.4 M sodium perchlorate, pH 6.3
Detection: UV at 214 nm Sample cooling: 5±3° C.
Column temperature: 22±5° C.
Injection volume: 10 µl for 0.5 mg/mL sample diluted in 1×PBS (Dulbecco's PBS, Life Technologies, USA) Analysis time: 15 min
Analysis software: Chromeleon Client software version 6.80SR8 Build 2623

A2—Hydrophobic Interaction Chromatography (HIC)

HIC analysis of the formulations 1-4 and the control formulation was performed on a HP1100 system equipped with an UV detector (Agilent Technology, USA).

Prior to injection the etanercept material at ~20 mg/ml was diluted 1+1 with sample dilution buffer containing 25 mM sodium phosphate pH 6.3 to ~10 mg/ml. Subsequently, a 1+1 mixture with Eluent A (binding buffer composed of 0.1 M sodium citrate and 0.8 M sodium sulfate, pH 6.0) to a final concentration of ~5 mg/ml was performed.

The following parameters were used analysis:
Column: TSKgel Ether-5PW (5.0×50 mm) (Tosoh Bioscience)
Eluent A: 0.1 M sodium citrate, 0.8 M sodium sulfate, pH 6.0
Eluent B: 0.1 M sodium citrate, 0.2 M sodium sulfate, pH 6.0
Sample dilution buffers: 25 mM sodium phosphate pH 6.3
Flow Rate: 0.5 ml/min
Injection Volume: 20 µL of 5 mg/ml etanercept material (0.1 mg etanercept)
Detection Wavelength: 280 nm
Column Thermostat: 40° C.
Gradient: step 1) 0% B for 4 min; step 2) 0% B to 100% B in 30 min
Column Storage: 20% ethanol at room temperature A3—Visual Inspection For visual inspection the syringes were inspected for the presence or absence of visible particles under gentle, manual, radial agitation for 5 seconds in front of a white and for 5 seconds in front of a black background according to the European Pharmacopoeia. The inspection was performed by two independent examiners. To further classify the particle content, the method described in the "Deutscher Arzneimittel-Codex" (DAC) was used. The classification can be described as follows:

No particles visible within 5 sec. 0 point
Several particles visible within 5 sec. 1 point
Particles clearly visible within 5 sec. 2 points
Large number of particles directly visible 10 points
Particles that are on the limit of being visible as distinct particles (cloudiness, schlieren . . . ) are rated with 2 points.

A4—UV-Vis Spectroscopy

UV-spectroscopy was performed using a Tecan Safire2 plate reader in 96-well plates at 280 nm. For each sample 3 wells (n=3), each with 200 µl solution at a concentration of 1 mg/ml were measured to minimize measurement errors. After the measurement, all data were subtracted by blank spectrum and corrected for the pathlength (A998 nm/A900 nm). Protein concentration was calculated using a specific absorbance coefficient of 1.13 at 280 nm for a protein concentration of 1.0 mg/ml at a pathlength of 1 cm. The concentration of etanercept was calculated using following formula:

$$A_{280\,nm} = \varepsilon_{280\,nm} \times C \times d$$

Where:
$A_{280\,nm}$=measured absorbance at 280 nm
$\varepsilon_{280\,nm}$=extinction coefficient at 280 nm in ml mg-1 cm-1 ($\varepsilon_{280\,nm}$=1.13 ml mg-1 cm-1)
C=concentration in mg/ml
d=pathlength in cm

A5—SDS-PAGE

SDS-PAGE was performed as follows.
In brief, for non-reducing conditions 40 µl of an etanercept sample (~1.0 mg/ml) were mixed with 50 µl of Tris Glycine Sample buffer (2×) and 10 µl of 10 mM maleimide solution. For reducing conditions 40 µl of an etanercept sample (~1.0 mg/ml) were mixed with 50 µl of Tris Glycine Sample buffer (2×) and 10 µl of 100 mg/ml DTT solution. Both samples were incubated in a heating block (Thermo Mixer Compact, Eppendorf AG, Germany) at 85° C. for 4 minutes prior to gel-loading. After heating, samples were cooled to RT and 12.5 µl of sample were then loaded in respective wells of Novex 4-20% Tris-Glycine gels (1 mm×12 wells, Life Technologies, USA). The gels were run at a constant current of 30 mA for ~60 minutes in an XCell SureLock Mini-Cell (Invitrogen, USA) in combination with a PowerPac 200 power supply (BioRad, USA). An aliquot of 10 µl SeeBlue Plus2 Pre-stained Protein Standard (Life Technologies, USA) was used as molecular weight marker.

After the gels were run, they were immediately freed from the cassettes and placed in 50 ml Simply Blue Stain Solution (Life Technologies, USA). The staining was conducted in a staining tray on a horizontal shaker (GFL 3012, Gesellschaft für Labortechnik, Germany) overnight. Destaining of gels was performed with highly purified water for a minimum of 3 hours including several washing steps (3× rinsing for 5 minutes with 50 ml highly purified water, and 5× rinsing for 15 minutes with 50 ml highly purified water).

Example 1—General Formulation Preparation Methods

Enbrel® reference market product (RMP, formulated at 50 mg/ml, 0.5 ml per syringe) was used to prepare all of the formulations described in this Example.

The material was withdrawn from the syringes into a sterile PETG bottle under laminar flow conditions by gently pushing the plungers. After pooling, visual inspection was performed by two examiners.

Four aliquots were prepared from the pooled bulk solution by transferring the material into sterile PETG bottles. The bottles have been placed at 2-8° C. for later phases of the project. 14 ml of the pooled solution were used for the formulations. 500 µl of the pooled material were additionally transferred into a polypropylene tube (Eppendorf) and stored at −80° C. for potential analytical purposes.

The RMP material was dialyzed into an amino acid free buffer containing 25 mM phosphate, 100 mM sodium chloride and 1% w/v sucrose at pH 6.3. Dialysis was performed at 4° C., using two slide-a-lyzer dialysis cassettes (Thermo Scientific) with a molecular weight cut-off of 10 kDa and up to 12 ml capacity. Afterwards both dialyzed etanercept fractions were pooled into a particle-free 15 ml PP tube (Greiner bio-one). Subsequently, visual inspection was performed by two examiners.

In addition, two additional dialysis preparations (i) and (ii) were performed overnight at 4° C. in slide-a-lyzer dialysis cassettes (Thermo Scientific) with a molecular weight cut-off of 10 kDa and up to 12 ml capacity.

The following buffers were prepared for these additional dialyses:
i) 25 mM citric acid
50 mM sodium chloride
pH 6.3
ii) 25 mM phosphate
50 mM sodium chloride
pH 6.3

After dialysis, the protein concentration was determined by UV 280 nm spectroscopy in 1:50 dilution.
i) 43.4 mg/ml; ii) 38.6 mg/ml The determined protein concentrations were taken into consideration during the preparation of the final formulations.

Formulations were transferred into particle-free 15 ml PP tubes (Greiner bio-one).

520 µl of either placebo or the pooled RMP at ~20 mg/ml were manually filled into 1 ml siliconized syringes (BD Hypak SCF combined with a 29G needle) under laminar air flow conditions. Particle free pipette tips (SafeSeal-Tips Professional, Biozym, Germany) were used for transferring the materials into the syringes. Intake of air bubbles was avoided by adding the liquid slowly to the syringe on the wall. The syringes were closed with plungers (HYPAK BSCF 1MLL W4023 FLUR DAIKYO LID) using a Bausch & Strobel SVP100 inserting and closing machine. The plungers were consistently placed at the same position such that a considerable headspace inside the syringes was created, enabling air-liquid interactions during mechanical stress.

The abovementioned procedures were employed in the preparation of the example formulations detailed in Table 1.

TABLE 1

Example Formulations

| No. | Buffer | pH | Salt | Sugar | Amino acid |
|---|---|---|---|---|---|
| 1 | 25 mM Phosphate | 6.3 | 100 mM NaCl | 1% Sucrose | — |
| 2 | 25 mM Phosphate | 6.3 | 100 mM NaCl | 1% Sucrose | 25 mM Aspartic acid |
| 3 | 25 mM Citrate | 6.3 | 100 mM NaCl | 1% Sucrose | 25 mM Histidine |
| 4 | 25 mM Phosphate | 6.3 | 50 mM NaCl | 4% Sucrose | 12.5 mM Lys + 12.5 mM Pro |
| Ctrl | 25 mM Phosphate | 6.3 | 100 mM | 1% Sucrose | 25 mM Arginine hydrochloride |

Formulation 1

Dialyzed Enbrel RMP material was diluted to ~20 mg/ml using sterile filtered buffer composed of 25 mM phosphate, 100 mM NaCl, 1% w/v sucrose at pH 6.3. No pH adjustment was required. This produced a final aqueous liquid formulation containing:
  20 mg/mL etanercept
  25 mM phosphate buffer;
  100 mM NaCl;
  1% w/v sucrose
at pH 6.3.

Formulation 2

Enbrel RMP material was dialyzed using sterile filtered buffer composed of 25 mM phosphate, 100 mM NaCl, 1% w/v sucrose at pH 6.3 to ultimately yield ~40 mg/ml etanercept in said buffer solution. A separate 50 mM aspartate/aspartic acid solution, pH 6.3, was formed within the same sterile filtered buffer described above. This 50 mM aspartate/aspartic acid solution was then spiked (1:1 dilution RMP:amino acids solution) into the RMP solution to achieve a final aspartate/aspartic acid concentration of 25 mM and a final RMP concentration of ~20 mg/ml. No pH adjustment was required. This produced a final aqueous liquid formulation containing:
  20 mg/mL etanercept
  25 mM phosphate buffer;
  100 mM NaCl;
  1% w/v sucrose;
  25 mM aspartic acid;
at pH 6.3.

Formulation 3

Dialyzed Enbrel RMP material from dialysis (i) was diluted to ~20 mg/ml using sterile filtered buffer to a final composition of 25 mM citrate, 100 mM NaCl, 1% sucrose and 25 mM histidine at pH 6.3. This produced a final aqueous liquid formulation containing:
  20 mg/mL etanercept
  25 mM citrate buffer;
  100 mM NaCl;
  1% w/v sucrose;
  25 mM histidine;
at pH 6.3.

Formulation 4

Dialyzed Enbrel RMP material from dialysis (ii) was diluted to ~20 mg/ml using sterile filtered buffer to a final composition of 25 mM phosphate, 50 mM NaCl, 4% sucrose and 12.5 mM lysine+12.5 mM proline at pH 6.3. This produced a final aqueous liquid formulation containing:
  20 mg/mL etanercept
  25 mM phosphate buffer;
  50 mM NaCl;
  4% w/v sucrose;
  12.5 mM lysine;
  12.5 mM proline;
at pH 6.3.

Control Formulation

Dialyzed Enbrel RMP material was diluted to ~40 mg/ml using sterile filtered buffer composed of 25 mM phosphate, 100 mM NaCl, 1% w/v sucrose at pH 6.3. A 50 mM L-Arg HCl solution, pH 6.3, was spiked (1:1 dilution RMP:amino acids solution) into the RMP solution to achieve a final amino acid concentration of 25 mM and a final RMP concentration of ~20 mg/ml. No pH adjustment was required. This produced a final aqueous liquid formulation containing:
  20 mg/mL etanercept
  25 mM phosphate buffer;
  100 mM NaCl;
  1% w/v sucrose;
  25 mM L-arginine hydrochloride;
at pH 6.3.

Example 2—Formulation Analysis and Stability Studies

The formulations of Table 1 were subjected to analysis via the analytical methods A1-A5 described above. The results of these analytical tests are presented in tabulated form below. Each test result relates to 1 of 4 samples selected from $T_o$ (samples not subjected to any stress), $T_{mech}$ (samples subjected to mechanical stress), $T_{heat}$ (samples subjected to heat stress), $T_{1\ month}$ (samples stored at room temperature for 1 month).

A1—Results from High Performance Size Exclusion Chromatography (HP-SEC)

TABLE 2

High Performance Size Exclusion Chromatography (HP-SEC)

| | | Relative Peak Area (%) | | |
|---|---|---|---|---|
| Formulation | Time Point | HMW | monomer | LMW |
| 1 | T0 | 2.6 | 95.6 | 1.8 |
| | T-mech | 2.9 | 95.3 | 1.8 |
| | T-heat | 2.7 | 85.6 | 11.8 |
| | T-1 month | 3.3 | 93.9 | 2.8 |
| 2 | T0 | 2.7 | 95.6 | 1.8 |
| | T-mech | 2.9 | 95.2 | 1.9 |
| | T-heat | 2.7 | 86 | 11.2 |
| | T-1 month | 3.2 | 94 | 2.8 |

TABLE 2-continued

High Performance Size Exclusion Chromatography (HP-SEC)

| Formulation | Time Point | HMW | monomer | LMW |
|---|---|---|---|---|
| 3 | T0 | 3.3 | 95 | 1.7 |
|  | T-mech | 3.4 | 95.0 | 1.7 |
|  | T-heat | 3.0 | 92.3 | 4.7 |
|  | T-1 month | 2.8 | 92.5 | 4.7 |
| 4 | T0 | 3.3 | 95.1 | 1.6 |
|  | T-mech | 3.4 | 95.1 | 1.6 |
|  | T-heat | 3.1 | 91.9 | 5.0 |
|  | T-1 month | 2.9 | 91.7 | 5.4 |
| Control | T0 | 2.6 | 95.6 | 1.8 |
|  | T-mech | 3.1 | 95.2 | 1.7 |
|  | T-heat | 2.6 | 85.7 | 11.7 |
|  | T-1 month | 3.1 | 94.1 | 2.8 |

A2—Results from Hydrophobic Interaction Chromatography (HIC)

TABLE 3

Hydrophobic Interaction Chromatography (HIC) Analysis

| Formulation | Time point | Truncated 1 | Truncated 2 | Monomer | Aggregate |
|---|---|---|---|---|---|
| Control | T0 | 0.3 | 2.0 | 85.1 | 12.6 |
|  | T-mech | 0.3 | 2.0 | 85.6 | 12.2 |
|  | T-heat | 0.3 | 5.2 | 82.4 | 12.1 |
|  | T-1 month | 0.3 | 2.6 | 85.0 | 12.2 |
| 1 | T0 | 0.2 | 2.2 | 85.5 | 12.1 |
|  | T-mech | 0.3 | 2.2 | 85.2 | 12.4 |
|  | T-heat | 0.2 | 5.7 | 82.4 | 11.7 |
|  | T-1 month | 0.2 | 2.5 | 85.2 | 12.2 |
| 2 | T0 | 0.2 | 2.1 | 85 | 12.7 |
|  | T-mech | 0.2 | 2 | 85.4 | 12.4 |
|  | T-heat | 0.2 | 5.5 | 82.5 | 11.8 |
|  | T-1 month | 0.2 | 2.5 | 85.3 | 12 |
| 3 | T0 | 0.4 | 1.6 | 87.5 | 10.5 |
|  | T-mech | 0.4 | 1.7 | 87 | 11 |
|  | T-heat | 0.5 | 2.4 | 86 | 11.2 |
|  | T-1 month | 0.3 | 1.8 | 85.4 | 12.6 |
| 4 | T0 | 0.4 | 1.7 | 87 | 11 |
|  | T-mech | 0.4 | 1.9 | 87 | 10.7 |
|  | T-heat | 0.4 | 2.4 | 85.8 | 11.5 |
|  | T-1 month | 0.3 | 2 | 85.8 | 11.9 |

A3—Results from Visual Inspection

TABLE 4

Visual Inspection Results

| Formulation | T0 | Tmech | Theat | T1 month |
|---|---|---|---|---|
| 1 | 10/10 | 1/2 | 2/2 | 2/2 |
|  | 10/10 | 1/2 | 10/10 | 2/2 |
| 2 | 2/2 | 2/10 | 2/10 | 2/2 |
|  | 1/2 | 1/2 | 10/10 | 0/0 |
| 3 | 10/1 | 0/1 | 10/1 | 10*/10 |
|  | 2#/0 | 1/1 | 10/1 | 10*/10 |
| 4 | 10/1 | 10/10 | 10/2 | 10/10 |
|  | 10/2 | 2/10 | 10/10 | 10/10 |
| Control | 10/10 | 2/10# | 10/2 | 0/0 |
|  | 10/10 | 1/1# | 10/10 | 2#/0 |

*fibers;
turbid

A4—Results from UV-Vis Spectroscopy

TABLE 5

Results of UV-Vis spectroscopic analysis

Protein concentration [mg/ml] determined in well plate or a cuvette/well plate

| Formulation | T0 | Tmech | Theat | T1 month |
|---|---|---|---|---|
| 1 | 17.5 | 17.9 | 18.3 | 20.3 |
| 2 | 18.0 | 17.7 | 17.9 | 20.5 |
| 3 | 21.2 | 22.1 | 20.3 | 20.9 |
| 4 | 20.4 | 22.1 | 19.2 | 20.5 |
| Control | 18.6 | 17.9 | 17.7 | 20.1 |

A5—Results from SDS-PAGE

TABLE 6

Results of SDS-PAGE analysis

| Formulation | Time point | Non reducing conditions | | | Reducing conditions | |
|---|---|---|---|---|---|---|
|  |  | MW [kDa] | Purity % | HMW [%] | LMW [%] | MW [kDa] | Purity % |
| 1 | T0 | 133 | 91.9 | 6.2 | 2.8 | 69 | 96.5 |
|  | T-mech | 132 | 92.4 | 4.5 | 3.2 | 70 | 97.8 |
|  | T-heat | 130 | 90.1 | 6.5 | 3.5 | 70 | 97.9 |
|  | T-1 month | 134 | 94.6 | 1.4 | 4.1 | 68 | 98.9 |
| 2 | T0 | 133 | 92.5 | 4.5 | 3.1 | 68 | 97.3 |
|  | T-mech | 133 | 92.9 | 4.2 | 3.0 | 72 | 98.1 |
|  | T-heat | 130 | 88.7 | 7.6 | 3.8 | 72 | 97.7 |
|  | T-1 month | 134 | 94.5 | 1.3 | 4.3 | 69 | 99.0 |
| 3 | T0 | 137 | 98.2 | 0.7 | 1.1 | 65 | 99.1 |
|  | T-mech | 135 | 97.5 | 1.4 | 1.2 | 70 | 99.2 |
|  | T-heat | 139 | 90.7 | 5.9 | 3.5 | 70 | 96.6 |
|  | T-1 month | 138 | 94.6 | 2.2 | 3.3 | 69 | 98.9 |
| 4 | T0 | 139 | 98.3 | 0.3 | 1.4 | 66 | 99.4 |
|  | T-mech | 136 | 96.3 | 1.6 | 2.2 | 72 | 98.1 |
|  | T-heat | 140 | 90.9 | 5.2 | 4.0 | 72 | 96.8 |
|  | T-1 month | 141 | 94.4 | 2.4 | 3.3 | 70 | 98.9 |
| Control | T0 | 131 | 90.7 | 6.4 | 3.0 | 71 | 96.4 |
|  | T-mech | 132 | 94.0 | 2.9 | 3.1 | 71 | 98.2 |
|  | T-heat | 131 | 86.4 | 10.6 | 3.1 | 71 | 98.0 |
|  | T-1 month | 132 | 92.1 | 2.5 | 5.5 | 70 | 99.2 |

Example 3—General Formulation Preparation Methods

Enbrel® reference market product (RMP, formulated at 50 mg/ml, 0.5 ml per syringe) was used to prepare the control formulation described in this Example.

This RMP material for the control formulation was pooled into a 15 ml Falcon tube under laminar air flow conditions. Pooling was gently performed through the primary needle attached to the RMP syringes, in order to avoid the formation of air bubbles. The pooled RMP material was dialyzed against a buffer containing 25 mM Arginine-HCl, 25 mM phosphate, 100 mM sodium chloride and 1% w/v sucrose at pH 6.3. Dialysis was performed at 2-8° C., using slide-a-lyzer dialysis cassettes (Thermo Scientific) with a molecular weight cut-off of 10 kDa and up to 12 ml capacity. The dialized RMP material was filtered (sterilely) using 0.22 μm PVDF syringe filters. The final concentration of Enbrel® in the control formulation was adjusted to 20 mg/ml and 50 mg/ml using a buffer containing 25 mM Arginine-HCl, 25 mM phosphate, 100 mM sodium chloride and 1% w/v sucrose at pH 6.3.

In addition, etanercept drug substance other than the RMP material was used to prepare all other formulations in this Example. A solution of the etanercept drug substance was first concentrated using an Amicon Ultra-15 centrifugal concentrator with a molecular weight cut-off of 30 kDa to obtain an aqueous solution containing etanercept at a concentration of approximately 70 mg/ml.

The abovementioned procedures were employed for the preparation of the example formulations detailed in Table 7.

TABLE 7

Example Formulations (each at 20 and 50 mg/ml protein concentration)

| No. | Buffer | pH | Salt | Sugar | Amino acid |
|---|---|---|---|---|---|
| A | 25 mM Phosphate | 6.3 | 100 mM NaCl | 1% Sucrose | 25 mM L-Aspartic acid |
| B | 25 mM Phosphate | 6.3 | 50 mM NaCl | 4% Sucrose | 12.5 mM L-Lys + 12.5 mM L-Pro |
| C | 25 mM Phosphate | 6.3 | 100 mM NaCl | 1% Sucrose | — |
| D | 25 mM Citrate | 6.3 | 100 mM NaCl | 1% Sucrose | 25 mM Histidine |
| Ctrl | 25 mM Phosphate | 6.3 | 100 mM | 1% Sucrose | 25 mM L-Arginine hydrochloride |

Formulation A

The aqueous solution of etanercept material was dialyzed using a sterile filtered buffer composed of 25 mM phosphate, 100 mM NaCl, 1% w/v sucrose, and 25 mM L-Aspartic acid at pH 6.3 to ultimately yield 55.7 mg/ml etanercept in said buffer solution. The so obtained dialyzed etanercept solution was diluted with the same sterile filtered buffer to result in a liquid formulation containing 20 mg/ml etanercept and a liquid formulation containing 50 mg/ml etanercept. This produced a final aqueous liquid formulation (Formulation A—20 mg/ml) containing:
  20 mg/mL etanercept
  25 mM phosphate buffer;
  100 mM NaCl;
  1% w/v sucrose;
  25 mM aspartic acid;
  at pH 6.3,
and a final aqueous liquid formulation (Formulation A—50 mg/ml) containing:
  50 mg/mL etanercept
  25 mM phosphate buffer;
  100 mM NaCl;
  1% w/v sucrose;
  25 mM aspartic acid;
  at pH 6.3.

Formulation B

The aqueous solution of etanercept material was dialyzed using sterile filtered buffer composed of 25 mM phosphate, 50 mM NaCl, 4% w/v sucrose, 12.5 mM L-Lysine HCl, and 12.5 mM L-Proline at pH 6.3 to ultimately yield 63.9 mg/ml etanercept in said buffer solution. The so obtained dialyzed etanercept solution was diluted with the same sterile filtered buffer to result in a liquid formulation containing 20 mg/ml etanercept and a liquid formulation containing 50 mg/ml etanercept. This produced a final aqueous liquid formulation (Formulation B—20 mg/ml) containing:
  20 mg/mL etanercept
  25 mM phosphate buffer;
  50 mM NaCl;
  4% w/v sucrose;
  12.5 mM lysine;
  12.5 mM proline;
  at pH 6.3,
and a final aqueous liquid formulation (Formulation B—50 mg/ml) containing:
  50 mg/mL etanercept
  25 mM phosphate buffer;
  100 mM NaCl;
  1% w/v sucrose;
  12.5 mM lysine;
  12.5 mM proline;
  at pH 6.3

Formulation C

The aqueous solution of etanercept material was dialyzed using a sterile filtered buffer composed of 25 mM phosphate, 100 mM NaCl, 1% w/v sucrose at pH 6.3 to ultimately yield 60.5 mg/ml etanercept in said buffer solution. The so obtained dialyzed etanercept solution was diluted with the same sterile filtered buffer to result in a liquid formulation containing 20 mg/ml etanercept and a liquid formulation containing 50 mg/ml etanercept. This produced a final aqueous liquid formulation (Formulation C—20 mg/ml) containing:
  20 mg/mL etanercept
  25 mM phosphate buffer;
  100 mM NaCl;
  1% w/v sucrose;
  at pH 6.3,
and a final aqueous liquid formulation (Formulation C—50 mg/ml) containing:
  50 mg/mL etanercept
  25 mM phosphate buffer;
  100 mM NaCl;
  1% w/v sucrose;
  at pH 6.3.

Formulation D

The aqueous solution of etanercept material was dialyzed using a sterile filtered buffer composed of 25 mM citrate, 100 mM NaCl, 1% w/v sucrose, and 25 mM L-Histidine at pH 6.3 to ultimately yield 59.8 mg/ml etanercept in said buffer solution. The so obtained dialyzed etanercept solution was diluted with the same sterile filtered buffer to result in a liquid formulation containing 20 mg/ml etanercept and a liquid formulation containing 50 mg/ml etanercept. This produced a final aqueous liquid formulation (Formulation D—20 mg/ml) containing:
  20 mg/mL etanercept
  25 mM citrate buffer;
  100 mM NaCl;
  1% w/v sucrose;
  25 mM histidine;
  at pH 6.3,
and a final aqueous liquid formulation (Formulation D—50 mg/ml) containing:
  50 mg/mL etanercept
  25 mM phosphate buffer;
  100 mM NaCl;

1% w/v sucrose;
25 mM histidine;
at pH 6.3.

Control Formulation

Dialyzed Enbrel RMP material at ~60 mg/ml in sterile filtered buffer composed of 25 mM phosphate, 100 mM NaCl, 1% w/v sucrose, and 25 mM L-Arginine HCl at pH 6.3 was further diluted. This produced a final aqueous liquid formulation (Control—20 mg/ml) containing:

20 mg/mL etanercept
25 mM phosphate buffer;
100 mM NaCl;
1% w/v sucrose;
25 mM L-arginine hydrochloride;
at pH 6.3, and a final aqueous liquid formulation (Control—50 mg/ml) containing:

50 mg/mL etanercept
25 mM phosphate buffer;
100 mM NaCl;
1% w/v sucrose;
25 mM L-arginine hydrochloride;
at pH 6.3.

510 μl of either control (RMP material) or etanercept drug substance at 20 mg/ml or 50 mg/ml were manually filled into 1 ml siliconized syringes (BD Hypak SCF combined with a 29G needle) under laminar air flow conditions. Particle free pipette tips (SafeSeal-Tips Professional, Biozym, Germany) were used for transferring the materials into the syringes. Intake of air bubbles was avoided by adding the liquid slowly to the syringe on the wall. The syringes were closed with plungers (HYPAK BSCF 1MLL W4023 FLUR DAI-KYO LID) using a Bausch & Strobel SVP100 inserting and closing machine. The plungers were consistently placed at the same position such that a considerable headspace inside the syringes was created, enabling air-liquid interactions during mechanical stress.

Example 4—Formulation Analysis and Stability Studies

The formulations of Table 7 were subjected to analysis via the analytical methods A1-A5 described above. The results of these analytical tests are presented in tabulated form below. Each test result relates to 1 of 5 samples selected from $T_o$ (samples not subjected to any stress), $T_{mech}$ (samples subjected to mechanical stress), $T_{heat}$ (samples subjected to heat stress), $T_{1\ month}$ (samples stored at room temperature for 1 month), and $T_{3\ month}$ (samples stored at room temperature for 3 months).

A1—Results from High Performance Size Exclusion Chromatography (HP-SEC)

TABLE 8

High Performance Size Exclusion Chromatography (HP-SEC) with formulations containing 20 mg/ml etanercept.

| Formulation | Time Point | Relative Peak Area (%) | |
|---|---|---|---|
| | | HMW | monomer |
| Formulation A 20 mg/ml | T0 | 0.6 | 99.4 |
| | T-mech | 0.6 | 99.4 |
| | T-heat | 1.0 | 99.0 |
| | T-1 month | 0.8 | 99.2 |
| | T-3 month | 1.2 | 98.8 |
| Formulation B 20 mg/ml | T0 | 0.6 | 99.4 |
| | T-mech | 0.6 | 99.4 |
| | T-heat | 1.0 | 99.0 |
| | T-1 month | 0.8 | 99.2 |
| | T-3 month | 1 | 99.0 |
| Formulation C 20 mg/ml | T0 | 0.6 | 99.4 |
| | T-mech | 0.6 | 99.4 |
| | T-heat | 1.0 | 99.0 |
| | T-1 month | 0.8 | 99.2 |
| | T-3 month | 1.2 | 98.8 |
| Formulation D 20 mg/ml | T0 | 0.6 | 99.4 |
| | T-mech | 0.5 | 99.5 |
| | T-heat | 0.6 | 99.4 |
| | T-1 month | 0.6 | 99.4 |
| | T-3 month | 0.7 | 99.3 |
| Control 20 mg/ml | T0 | 3.2 | 96.8 |
| | T-mech | 3.2 | 96.8 |
| | T-heat | 3.6 | 96.4 |
| | T-1 month | 3.4 | 96.6 |
| | T-3 month | 3.4 | 96.6 |

TABLE 9

High Performance Size Exclusion Chromatography (HP-SEC) with formulations containing 50 mg/ml etanercept.

| Formulation | Time Point | Relative Peak Area (%) | |
|---|---|---|---|
| | | HMW | monomer |
| Formulation A 50 mg/ml | T0 | 0.6 | 99.4 |
| | T-mech | 0.6 | 99.4 |
| | T-heat | 1.5 | 98.5 |
| | T-1 month | 1.1 | 98.9 |
| | T-3 month | 1.8 | 98.2 |
| Formulation B 50 mg/ml | T0 | 0.6 | 99.4 |
| | T-mech | 0.6 | 99.4 |
| | T-heat | 1.4 | 98.6 |
| | T-1 month | 1.0 | 99.0 |
| | T-3 month | 1.6 | 98.4 |
| Formulation C 50 mg/ml | T0 | 0.6 | 99.4 |
| | T-mech | 0.6 | 99.4 |
| | T-heat | 1.5 | 98.5 |
| | T-1 month | 1.2 | 98.8 |
| | T-3 month | 1.8 | 98.2 |
| Formulation D 50 mg/ml | T0 | 0.6 | 99.4 |
| | T-mech | 0.6 | 99.4 |
| | T-heat | 1.0 | 99.0 |
| | T-1 month | 0.8 | 99.2 |
| | T-3 month | 1.1 | 98.9 |
| Control 50 mg/ml | T0 | 3.2 | 96.8 |
| | T-mech | 3.3 | 96.7 |
| | T-heat | 4.2 | 95.8 |
| | T-1 month | 3.6 | 96.4 |
| | T-3 month | 4.0 | 96.0 |

TABLE 10

Monomer content HP-SEC/SDS-PAGE*

| Formulation | T0 | T-heat | T-1 month | T-3 month |
|---|---|---|---|---|
| Control 20 mg/ml | 94.8 | 93.8 | 95.1 | 92.8 |
| Control 50 mg/ml | 94.7 | 92.0 | 93.3 | 92.0 |
| Form. A 20 mg/ml | 96.3 | 95.6 | 96.8 | 92.6 |
| Form. A 50 mg/ml | 96.4 | 93.2 | 94.2 | 91.8 |

TABLE 10-continued

Monomer content HP-SEC/SDS-PAGE*

| Formulation | T0 | T-heat | T-1 month | T-3 month |
|---|---|---|---|---|
| Form. B 20 mg/ml | 96.4 | 95.3 | 96.4 | 91.7 |
| Form. B 50 mg/ml | 96.3 | 94.3 | 94.4 | 91.8 |
| Form. C 20 mg/ml | 96.2 | 95.2 | 96.1 | 91.5 |
| Form. C 50 mg/ml | 96.3 | 94.0 | 93.7 | 91.1 |
| Form. D 20 mg/ml | 96.4 | 95.7 | 95.4 | 93.6 |
| Form. D 50 mg/ml | 96.1 | 95.3 | 95.0 | 92.3 |

*(Calculated as 100-HMWs % (from SEC) – LMWs % (from SDS-PAGE))

A2—Results from Hydrophobic Interaction Chromatography (HIC)

TABLE 11

Hydrophobic Interaction Chromatography (HIC) Analysis with formulations containing 20 mg/ml etanercept

| | | Relative peak area [%] | | | |
|---|---|---|---|---|---|
| Formulation | Time point | Peak 1.1 | Peak 1.2 | Peak 2 (main peak) Monomer | Peak 3 |
| Control 20 mg/ml | T0 | 0.0 | 1.5 | 88.7 | 9.8 |
| | T-mech | 0.1 | 1.5 | 89.1 | 9.5 |
| | T-heat | 0.0 | 2.4 | 87.7 | 9.9 |
| | T-1 month | 0.4 | 2.1 | 87.3 | 10.2 |
| | T-3 month | 0.7 | 3.1 | 85.6 | 10.6 |
| Formulation A 20 mg/ml | T0 | 0.0 | 2.2 | 97.8 | |
| | T-mech | 0.0 | 2.2 | 97.7 | |
| | T-heat | 0.0 | 3.3 | 96.7 | |
| | T-1 month | 0.5 | 2.8 | 96.7 | |
| | T-3 month | 0.6 | 4.4 | 95.0 | |
| Formulation B 20 mg/ml | T0 | 0.0 | 2.4 | 97.6 | |
| | T-mech | 0.0 | 2.2 | 97.9 | |
| | T-heat | 0.0 | 3.5 | 96.5 | |
| | T-1 month | 0.5 | 2.9 | 96.7 | |
| | T-3 month | 0.7 | 4.5 | 94.5 | |
| Formulation C 20 mg/ml | T0 | 0.0 | 2.4 | 97.6 | |
| | T-mech | 0.0 | 2.3 | 97.7 | |
| | T-heat | 0.0 | 3.9 | 96.2 | |
| | T-1 month | 0.5 | 3.2 | 96.3 | |
| | T-3 month | 0.9 | 5.6 | 93.6 | |
| Formulation D 20 mg/ml | T0 | 0.0 | 2.5 | 97.6 | |
| | T-mech | 0.0 | 2.3 | 97.7 | |
| | T-heat | 0.0 | 3.0 | 97.1 | |
| | T-1 month | 0.4 | 2.5 | 97.0 | |
| | T-3 month | 0.6 | 4.0 | 95.3 | |

TABLE 12

Hydrophobic Interaction Chromatography (HIC) Analysis with formulations containing 50 mg/ml etanercept

| | | Relative peak area [%] | | | |
|---|---|---|---|---|---|
| Formulation | Time point | Peak 1.1 | Peak 1.2 | Peak 2 (main peak) Monomer | Peak 3 |
| Control 50 mg/ml | T0 | 0.0 | 1.6 | 88.4 | 10.0 |
| | T-mech | 0.1 | 1.5 | 89.1 | 9.4 |
| | T-heat | 0.1 | 2.5 | 86.6 | 10.9 |
| | T-1 month | 0.4 | 2.0 | 87.4 | 10.2 |
| | T-3 month | 0.7 | 3.1 | 85.6 | 10.5 |
| Formulation A 50 mg/ml | T0 | 0.0 | 2.1 | 97.9 | |
| | T-mech | 0.0 | 2.2 | 97.8 | |
| | T-heat | 0.0 | 3.3 | 96.7 | |
| | T-1 month | 0.5 | 2.8 | 96.7 | |
| | T-3 month | 0.7 | 4.5 | 94.8 | |
| Formulation B 50 mg/ml | T0 | 0.0 | 2.1 | 97.9 | |
| | T-mech | 0.0 | 2.3 | 97.7 | |
| | T-heat | 0.0 | 3.5 | 96.5 | |
| | T-1 month | 0.5 | 2.8 | 96.7 | |
| | T-3 month | 0.7 | 5.0 | 94.3 | |
| Formulation C 50 mg/ml | T0 | 0.0 | 2.4 | 97.6 | |
| | T-mech | 0.0 | 2.3 | 97.7 | |
| | T-heat | 0.0 | 3.7 | 96.3 | |
| | T-1 month | 0.5 | 3.2 | 96.3 | |
| | T-3 month | 0.8 | 5.4 | 93.8 | |
| Formulation D 50 mg/ml | T0 | 0.0 | 2.5 | 97.6 | |
| | T-mech | 0.0 | 2.2 | 97.8 | |
| | T-heat | 0.0 | 2.9 | 97.1 | |
| | T-1 month | 0.4 | 2.6 | 97.0 | |
| | T-3 month | 0.6 | 4.0 | 95.4 | |

A3—Results from Visual Inspection

TABLE 13

Visual Inspection Results

| Formulation | T0 | Tmech | Theat | T1 month | T3 month |
|---|---|---|---|---|---|
| Control 20 mg/ml | 0/0 | 1/0 | 0/1 | 1/0 | 0/1 |
| | | 0/0 | 0/0 | 2*/1* | 0/0 |
| Control 50 mg/ml | 0/0 | 0/0 | 0/0 | 2*/1* | 2*/2* |
| | | 0/0 | 0/0 | 1/0 | 1/1 |
| Formulation A 20 mg/ml | 0/0 | 0/1 | 0/0 | 0/0 | 0/0 |
| | | 0/1 | 0/0 | 1/2 | 1/2* |
| Formulation A 50 mg/ml | 0/0 | 0/0 | 1/0 | 0/0 | 0/1 |
| | | 0/0 | 0/0 | 1/0 | 0/1 |
| Formulation B 20 mg/ml | 1/0 | 0/0 | 2*/0 | 1/1 | 0/0 |
| | | 0/0 | 0/0 | 1/0 | 0/0 |
| Formulation B 50 mg/ml | 0/0 | 0/0 | 0/0+ | 0/0 | 1/0 |
| | | 0/0 | | 0/0 | 0/0 |
| Formulation C 20 mg/ml | 0/0 | 0/0 | 0/1 | 0/0 | 1/0 |
| | | 0/0 | 0/0 | 1/0 | 0/0 |
| Formulation C 50 mg/ml | 0/0 | 0/0 | 1/0 | 0/0 | 2*/2* |
| | | 0/0 | 0/0 | 1/1 | 2*/2* |
| Formulation D 20 mg/ml | 0/0 | 1/0 | 1/0 | 0/0 | 0/0 |
| | | 0/0 | 0/0 | 0/0 | 0/0 |
| Formulation D 50 mg/ml | 0/0 | 0/0 | 0/0 | 0/0 | 0/0 |
| | | 0/0 | 0/0 | 0/0 | 0/1 |

*fibers;
+only one syringe

A5—Results from SDS-PAGE

TABLE 14

Results of SDS-PAGE analysis

| | | Non reducing conditions | | | Reducing conditions |
|---|---|---|---|---|---|
| Formulation | Time point | Purity % | HMW [%] | LMW [%] | Purity% |
| Control 20 mg/ml | T0 | >92 | Present | 2.0 | >92 |
| | T-heat | >92 | Present | 2.6 | >92 |
| | T-1 month | >92 | Present | 1.5 | >92 |
| | T-3 month | >92 | Present | 3.8 | >96 |
| Control 50 mg/ml | T0 | >92 | Present | 2.1 | >92 |
| | T-heat | >92 | Present | 3.8 | >92 |
| | T-1 month | >92 | Present | 3.1 | >92 |
| | T-3 month | >92 | Present | 4.0 | >96 |

TABLE 14-continued

Results of SDS-PAGE analysis

| Formulation | Time point | Non reducing conditions | | | Reducing conditions Purity% |
|---|---|---|---|---|---|
| | | Purity % | HMW [%] | LMW [%] | |
| Formulation A 20 mg/ml | T0 | >92 | | 3.1 | >92 |
| | T-heat | >92 | | 3.4 | >92 |
| | T-1 month | >92 | | 2.4 | >92 |
| | T-3 month | >92 | | 6.2 | >96 |
| Formulation A 50 mg/ml | T0 | >92 | | 3.0 | >92 |
| | T-heat | >92 | | 5.3 | >92 |
| | T-1 month | >92 | | 4.7 | >92 |
| | T-3 month | >92 | | 6.4 | >96 |
| Formulation B 20 mg/ml | T0 | >92 | | 3.0 | >92 |
| | T-heat | >92 | | 3.7 | >92 |
| | T-1 month | >92 | | 2.8 | >92 |
| | T-3 month | >92 | | 7.3 | >96 |
| Formulation B 50 mg/ml | T0 | >92 | | 3.1 | >92 |
| | T-heat | >92 | | 4.3 | >92 |
| | T-1 month | >92 | | 4.6 | >92 |
| | T-3 month | >92 | | 6.6 | >96 |
| Formulation C 20 mg/ml | T0 | >92 | | 3.2 | >92 |
| | T-heat | >92 | | 3.8 | >92 |
| | T-1 month | >92 | | 3.1 | >92 |
| | T-3 month | >92 | | 7.3 | >96 |
| Formulation C 50 mg/ml | T0 | >92 | | 3.1 | >92 |
| | T-heat | >92 | | 4.5 | >92 |
| | T-1 month | >92 | | 5.1 | >92 |
| | T-3 month | >92 | | 7.1 | >96 |
| Formulation D 20 mg/ml | T0 | >92 | | 3.0 | >92 |
| | T-heat | >92 | | 3.7 | >92 |
| | T-1 month | >92 | | 4.0 | >92 |
| | T-3 month | >92 | | 5.7 | >96 |
| Formulation D 50 mg/ml | T0 | >92 | | 3.3 | >92 |
| | T-heat | >92 | | 3.7 | >92 |
| | T-1 month | >92 | | 4.2 | >92 |
| | T-3 month | >92 | | 6.6 | >96 |

LIST OF ABBREVIATIONS

A absorbance
Arg arginine
Asp aspartic acid
Glu glutamic acid
His histidine
Lys lysine
Pro proline
AUC area under the curve
cIEF capillary isoelectric focusing
DLS dynamic light scattering
DS drug substance
pDSC differential scanning calorimetry
DSF dynamic scanning fluorimetry
FNU formazin nephelometric unit
HIC hydrophobic interaction chromatography
HP-SEC high pressure size exclusion chromatography
MFI Micro-Flow Imaging
OD optical density
PDI polydispersity index
PETG polyethylene terephthalate glycol
PFS pre-filled syringes
Ph.Eur. European Pharmacopoeia
PP polypropylene
RMM resonant mass measurement
RMP reference market product (Enbrel®)
SDS-PAGE sodium dodecyl polyacrylamide gel electrophoresis
Tm melting temperature
UV ultraviolet

The invention claimed is:
1. A liquid pharmaceutical composition comprising:
    20 to 70 mg/mL etanercept (including any biosimilar thereof);
    10 to 40 mM buffer system, wherein the buffer system is a phosphate buffer system;
    20 to 150 mM sodium chloride;
    0.5 to 5.0 wt % sucrose; and
    a combination of lysine and proline;
wherein:
    the liquid pharmaceutical composition has a pH between pH 6.1 and 6.5;
    the liquid pharmaceutical composition is either free of arginine or comprises arginine in a concentration of at most 0.1 mM; and
    the liquid pharmaceutical composition is either free of sulphur-containing amino acid(s) or comprises sulphur-containing amino acid(s) in a concentration of at most 0.1 mM.
2. The liquid pharmaceutical composition of claim 1, wherein the molar ratio of lysine to proline is between 2:1 and 1:2.
3. The liquid pharmaceutical composition of claim 1, comprising lysine in combination with proline at a total amino acid concentration of from 10 to 40 mM.
4. The liquid pharmaceutical composition of claim 1, wherein the molar concentrations of sucrose and sodium chloride are interrelated by Equation (1):

$$[\text{stabiliser}]_{mol} * [\text{tonicifier}]_{mol} = A_{mol} * 2^n \quad \text{Equation (1)}$$

where $[\text{stabiliser}]_{mol}$ is the molar concentration of sucrose; $[\text{tonicifier}]_{mol}$ is the molar concentration of the sodium chloride; $A_{mol}$ is a baseline molar concentration constant; and n is any positive or negative number; wherein $A_{mol}$ is between 2000 and 4000 mM$^2$; and n is between −2 and +2.
5. The liquid pharmaceutical composition of claim 1, wherein the liquid pharmaceutical composition comprises:
    40-60 mg/mL (or alternatively 20-30 mg/mL) etanercept;
    20-30 mM buffer system, wherein the buffer system is a phosphate buffer system;
    40-120 mM sodium chloride;
    0.5-5.0 wt % sucrose; and
    water (for injection);
wherein the composition has a pH between pH 6.1 and 6.5; and
wherein the composition comprises
    a combination of 10-15 mM lysine and 10-15 mM proline; and
wherein the composition is either free of arginine or comprises arginine in a concentration of at most 0.1 mM;
wherein the composition is either free of sulphur-containing amino acid(s) or comprises sulphur-containing amino acid(s) in a concentration of at most 0.1 mM;
wherein the composition is either free of non-ionic surfactants or comprises one or more of said surfactants in a (collective) concentration of at most 0.1 mM; and
wherein the composition is either free of nitrogen-containing chelating agent(s) or comprises nitrogen-containing chelating agent(s) in a concentration of at most 0.1 mM.
6. The liquid pharmaceutical composition of claim 1, wherein the liquid pharmaceutical composition consists essentially of:
    40-60 mg/mL (or alternatively 20-30 mg/mL) etanercept;
    20-30 mM buffer system, wherein the buffer system is a phosphate buffer system;
    40-120 mM sodium chloride;
    0.5-5.0 wt % sucrose; and
    water (for injection);

wherein the composition has a pH between pH 6.2 and 6.4; and wherein the composition comprises a combination of 10-15 mM lysine and 10-15 mM proline.

7. The liquid pharmaceutical composition of claim 1, wherein the liquid pharmaceutical composition consists essentially of:

50 mg/mL (or alternatively 25 mg/mL) etanercept;

25 mM phosphate buffer system;

50 mM sodium chloride;

4 wt % (or 120 mM+/−4 mM) sucrose;

12.5 mM lysine;

12.5 mM proline; and water (for injection);

wherein the composition has a pH of 6.3.

8. A drug delivery device comprising a liquid pharmaceutical composition of claim 1.

9. A liquid pharmaceutical composition of claim 1 for use in therapy.

10. A liquid pharmaceutical composition claimed in claim 1 for use in the treatment of rheumatoid arthritis, juvenile rheumatoid arthritis, psoriatic arthritis, plaque psoriasis, and/or ankylosing spondylitis.

* * * * *